(12) United States Patent
Dalebout et al.

(10) Patent No.: US 8,216,156 B2
(45) Date of Patent: *Jul. 10, 2012

(54) SYSTEMS, METHODS, AND DEVICES FOR SAMPLING BODILY FLUID

(75) Inventors: Corey Dalebout, Lincoln, CA (US); Josh Sybrowsky, Lincoln, CA (US)

(73) Assignee: GluCor Systems, LLC, Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/030,012

(22) Filed: Feb. 17, 2011

(65) Prior Publication Data

US 2011/0166433 A1 Jul. 7, 2011

Related U.S. Application Data

(63) Continuation of application No. 12/036,787, filed on Feb. 25, 2008, now abandoned, which is a continuation-in-part of application No. 11/765,888, filed on Jun. 20, 2007, now abandoned.

(60) Provisional application No. 60/805,426, filed on Jun. 21, 2006.

(51) Int. Cl.
*B65D 81/00* (2006.01)
*A61B 5/00* (2006.01)

(52) U.S. Cl. ............ 600/584; 600/347; 600/576

(58) Field of Classification Search ........... 600/347, 600/573, 576, 587
See application file for complete search history.

(56) References Cited

U.S. PATENT DOCUMENTS

| | | |
|---|---|---|
| 3,115,138 A | 12/1963 | McElvenny et al. |
| 4,429,693 A | 2/1984 | Blake et al. |
| 4,673,386 A | 6/1987 | Gordon |
| 5,368,029 A | 11/1994 | Holcombe et al. |
| 5,374,401 A | 12/1994 | von Berg |
| 5,961,472 A | 10/1999 | Swendson et al. |
| 6,159,164 A | 12/2000 | Neese et al. |
| 6,224,561 B1 | 5/2001 | Swendson et al. |
| 6,394,979 B1 | 5/2002 | Sharp et al. |
| 6,616,632 B2 | 9/2003 | Sharp et al. |
| 6,623,702 B2 | 9/2003 | Allen et al. |
| 7,299,081 B2 | 11/2007 | Mace et al. |
| 2002/0185384 A1 | 12/2002 | Leong et al. |
| 2004/0116830 A1* | 6/2004 | Trudeau et al. ........... 600/584 |

(Continued)

OTHER PUBLICATIONS

Office Action mailed Aug. 18, 2010 under U.S. Appl. No. 12/036,787.

(Continued)

*Primary Examiner* — Max Hindenburg
*Assistant Examiner* — Emily Lloyd
(74) *Attorney, Agent, or Firm* — Workman Nydegger

(57) ABSTRACT

A fluid sampling system is disclosed comprising a fluid drawing device and a fluid sampling device. In one embodiment, the fluid sampling device has a base portion having a cannula, a handle, and a ridge extending around at least a portion of an outer surface. A top portion has a flange adapted to engage the ridge to couple the top portion to the base portion. In another embodiment, the fluid sampling device has a base portion having a cannula, a handle, a mounting portion, and a test strip coupled to the base portion at least partially within the mounting portion. In yet another embodiment, the fluid sampling device has a test strip housing for receiving an end of a test strip therein. Extending from an end of the test strip housing is a blunt cannula.

22 Claims, 18 Drawing Sheets

U.S. PATENT DOCUMENTS

| | | | |
|---|---|---|---|
| 2005/0136501 | A1 | 6/2005 | Kuriger |
| 2005/0277850 | A1 | 12/2005 | Mace et al. |
| 2007/0129618 | A1 | 6/2007 | Goldberger et al. |
| 2008/0045862 | A1 | 2/2008 | Dalebout et al. |
| 2008/0255473 | A1 | 10/2008 | Dalebout et al. |

OTHER PUBLICATIONS

Better Living Now, ACCU-CHECK Comfort Curve Test Strips [online], Apr. 16, 2006 [retrieved on Feb. 16, 2011]. Retrieved from internet: <URL: www.betterlivingnow.com/products/proddetail.cfm?ndc=50924038110>.

Office Action mailed Jan. 4, 2008, cited in related U.S. Appl. No. 11/765,888 (Attached).

Office Action mailed Jul. 9, 2008, cited in related U.S. Appl. No. 11/765,888 (Attached).

Office Action mailed Sep. 27, 2010, cited in related U.S. Appl. No. 12/252,041 (Attached).

Greet Van den Bergh, et. al., Intensive Insulin Therapy in Critically Ill Patients, The New England Journal of Medicine, vol. 345:1359-1367, No. 19, Nov. 8, 2001.

Aragon, Evaluation of Nursing Work Effort and Perceptions About Blood Glucose Testing in Tight Glycemic Control, American Journal of Critical Care, vol. 15:370-377, No. 4, Jul. 2006.

* cited by examiner

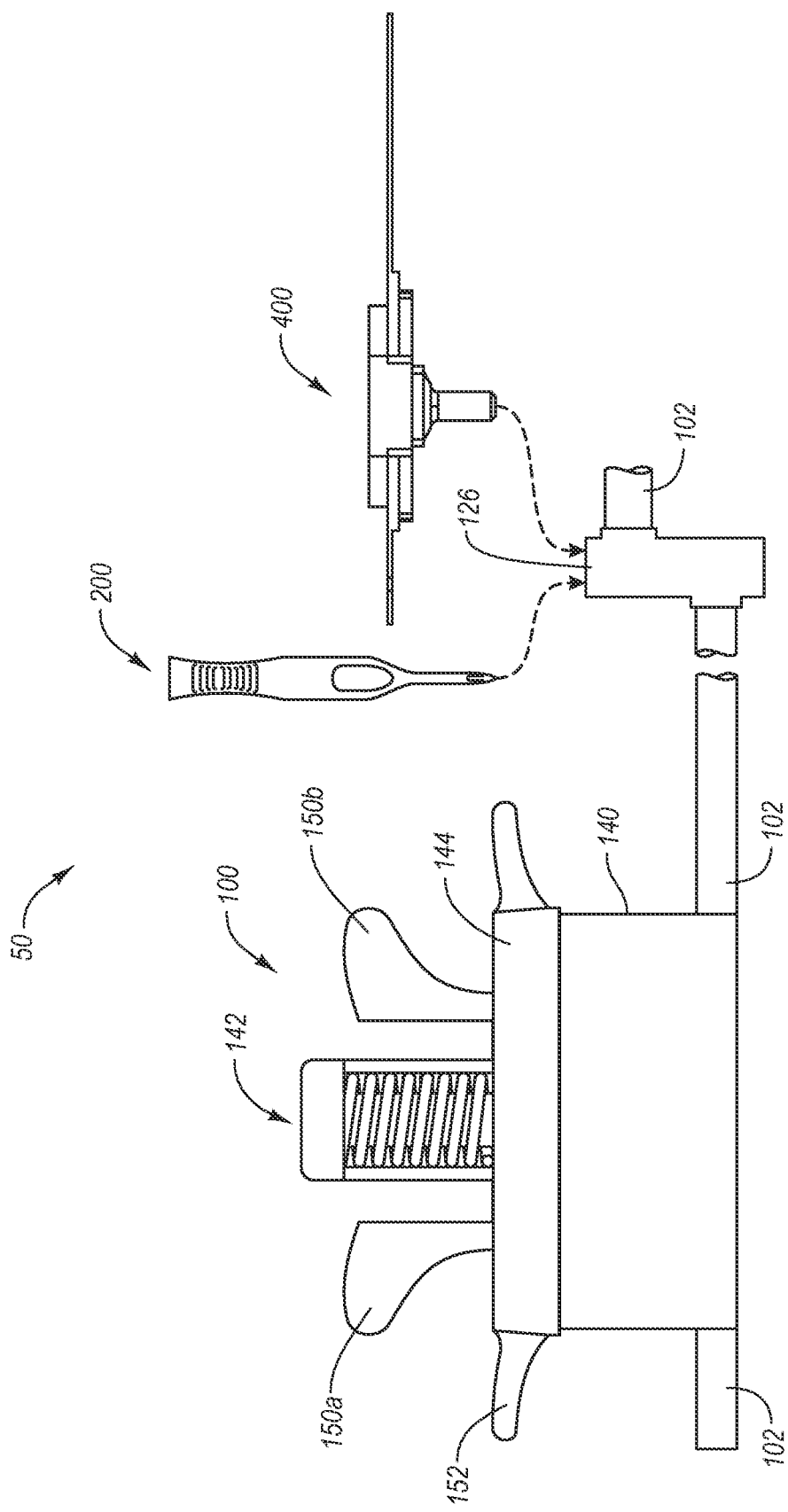

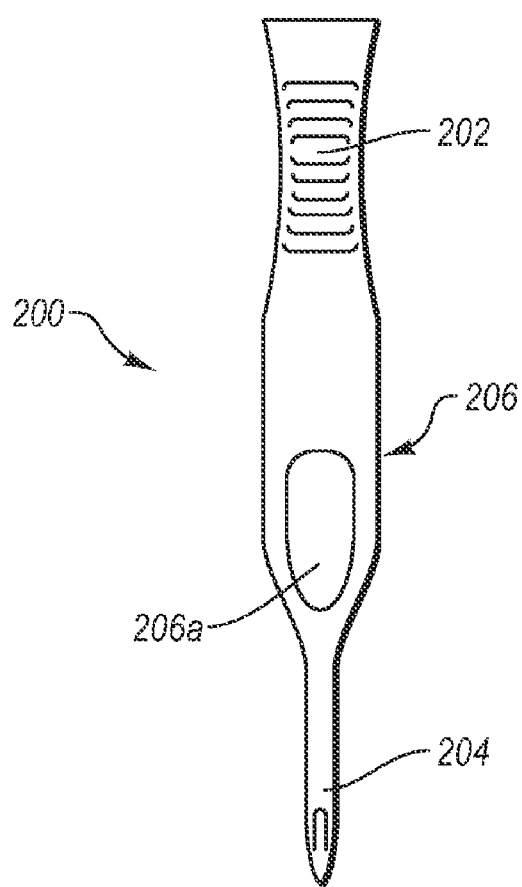
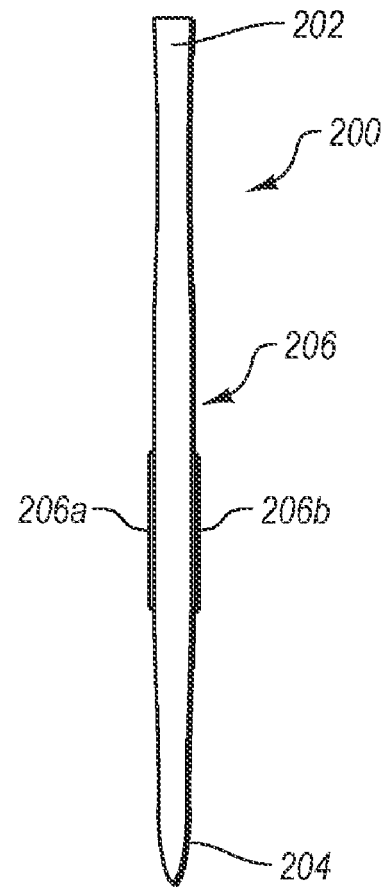
Fig. 4A
Fig. 4B

SYSTEMS, METHODS, AND DEVICES FOR SAMPLING BODILY FLUID

CROSS-REFERENCE TO RELATED APPLICATIONS

This application is a continuation of U.S. patent application Ser. No. 12/036,787 filed 25 Feb. 2008, now abandoned entitled SYSTEMS, METHODS AND DEVICES FOR SAMPLING BODILY FLUID, which is a continuation-in-part of U.S. patent application Ser. No. 11/765,888, filed Jun. 20, 2007, now abandoned entitled SYSTEMS, METHODS, AND DEVICES FOR SAMPLING BODILY FLUID, which claims the benefit of U.S. Provisional Application No. 60/805,426, filed Jun. 21, 2006, entitled BLOOD SAMPLING SYSTEM, all of which are hereby incorporated by reference in their entireties.

BACKGROUND OF THE INVENTION

1. The Field of the Invention

The invention relates to medical systems, methods, and devices, more specifically, the invention relates to a fluid sampling system.

2. Relevant Technology

In some medical procedures, the condition of a patient can require that an intravenous/intra-arterial tube or catheter be inserted into a blood vessel. The patient's blood vessel can be connected by the tube to a source of fluid which can provide fluid, such as a medicament, and which can also be connected to a pressure transducer that senses the pressure within the patient's blood vessel.

In critical care situations, it can be necessary to periodically obtain samples of the patient's bodily fluids, such as blood. For procedures carried out using a needle stick, the likelihood of a health care worker being inadvertently stuck can increase, thereby increasing the risk of infection from a contaminated needle. Rather than stick a patient with a needle each time blood must be drawn, blood can be drawn through the tube already connected to the patient's blood vessel. Since the tube connected to the patient's blood vessel can contain fluid other than blood, such as saline solution and some medication, it is useful to draw the patient's blood up into the tube so that a blood sample can be obtained which is substantially unadulterated by the fluid which is being supplied to the tube by an external source. After the substantially unadulterated blood has been drawn up the tube to a sampling site, the blood sample can be collected into a sample container.

Disadvantageously, many of the previously available devices require two-handed operation by a medical practitioner. Some of the previous devices utilize a conventional medical syringe to create the suction necessary to draw the blood up the tube. Such syringes are often unwieldy to use and their typical long, narrow dimensions makes them cumbersome. Many of the previously available devices are complicated and expensive. Moreover, some of the previously available devices include sharp bends in the fluid path and/or relatively long supplementary fluid paths both of which result in residual blood and fluid remaining in the fluid path which can cause problems such as clotting.

In 2001, a study of 1548 patients was performed to demonstrate the effects of "intensive insulin therapy" on mortality and morbidity. See Greet Van den Bergh, et. al., *Intensive Insulin Therapy in Critically Ill Patients*, The New England Journal of Medicine, Vol. 345:1359-1367, No. 19, Nov. 8, 2001. The study showed that patients with tightly controlled blood glucose levels (between 80-110mg/dl) had remarkably improved outcomes. Overall mortality was decreased by 34%, blood stream infections by 46%, acute renal failure requiring dialysis or hemofiltration decreased by 41%, the median number of red cell transfusions decreased by 50% as well as requiring less time on the ventilator and less days in the ICU. Beyond the increased health benefits to patients, this reduces hospital costs by $3000 to $4000 per ICU patient. See http://www.santacruzsentinel.com/archive/2005/February/13/biz/stories/02biz.htm.

The medical community has been striving for successful implementation of intensive insulin therapy because of the documented benefits of intensive insulin therapy. In order to implement this therapy, patients can have their fingers stuck for glucose readings every hour for days, weeks and even months. This has caused a significant amount of pain and torment to be inflicted to the patients. Additionally, repeated glucose level monitoring can take up valuable time of registered nurses (RNs) and practitioners.

BRIEF SUMMARY

Example embodiments of the medical system described herein can enable the user more freedom to deal with positional lines, obtain glucose readings and can save time by initiating the testing process. This system can accomplish various significant improvements over the prior art while still garnering the significant benefits of intensive insulin therapy and being adaptable to nearly all hospitals. One benefit of the present invention is that it can reduce pain and discomfort of patients by reducing repeated finger pricking and venous sticks to obtain lab samples. Further, the present invention can decrease the time necessary for practitioners to ascertain patient's glucose levels and obtain blood samples for lab use. Another benefit of the present invention is that it can decrease the risk to practitioners and patients by reducing the need for needles used in the transfer of blood from sample ports to the test strip, and those used with phlebotomy. Additionally, the present invention can decrease cross contamination risk by utilizing a contained blood sample within the sampling device.

Example of embodiments of the medical system of the present invention can include a medical device for drawing a patient's blood into an intravenous tube. The medical device can include a housing having a fill chamber into which a patient's blood can be drawn. The fill chamber can be in fluid communication with a patient injection site, such as a sample port of an intravenous tube. A piston can be positioned within the fill chamber. The outer edge of the piston and the interior walls of the fill chamber can be configured to substantially create a seal between the piston and the interior walls of the fill chamber. The piston can be moved from a first position to a second position, which can create a negative pressure within the fill chamber that can draw fluid from the patient injection site into the fill chamber. The present embodiment can also include biasing means, such as a spring or fluid pressure in the line or tube, for biasing the piston to the second position. The medical system can further include securing means, such as clamps, engaging ridges, and the like, for selectively securing the piston in the first and/or second positions.

The medical system can also include a medical device for sampling bodily fluid, such as blood. The fluid sampling device can comprise a base portion and a top portion. The base portion can include a blunt cannula that can be inserted into a sample port of an intravenous tube or catheter. The base portion can also have a handle for a user to hold and which facilitates use of the medical device. Extending around at least a portion of the base portion's outer edge can be a ridge that can be configured to engage the top portion. The top portion can include a flange adapted to engage the base portion's ridge in order to couple the top portion to the base portion. In some embodiments, the top portion and the base portion are designed to couple together with a test strip movably disposed therebetween. The fluid sampling device can also include a protective housing for preventing undesired damage or contamination of the fluid sampling device.

Alternative embodiments of a fluid sampling device can comprise a base portion and a test strip mounted thereon. The base portion can include a blunt cannula that can be inserted into a sample port of an intravenous tube or catheter. The base portion can have a handle for a user to hold and which facilitates use of the medical device. The top surface of the base portion can define a receiving portion adapted to receive the test strip. The test strip can be coupled or fastened to the base portion. The medical device can be adapted to direct the bodily fluid sample through the blunt cannula and onto the test strip. As noted, the fluid sampling device can also include a protective housing for preventing undesired damage or contamination of the fluid sampling device.

Another alternative embodiment of a fluid sampling device can comprise a test strip housing and a test strip at least partially disposed within the test strip housing. The test strip housing can include a blunt cannula that can be inserted into a sample port of an intravenous tube or catheter. The test strip housing can also have test strip receptacle with an interior portion adapted to receive the test strip therein. The test strip can be coupled or fastened within the test strip receptacle. The test strip receptacle and the blunt cannula can be coupled together with a connecting portion. The medical device can be adapted to direct the bodily fluid sample through the blunt cannula and onto the test strip.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 illustrates the fluid sampling system according to one embodiment of the present invention;

FIG. 4A illustrates a top view of a fluid sampling device according to one embodiment of the present invention;

FIG. 4B illustrates a side view of the fluid sampling device of FIG. 4A;

DETAILED DESCRIPTION OF THE PREFERRED EMBODIMENTS

Figure 2A:
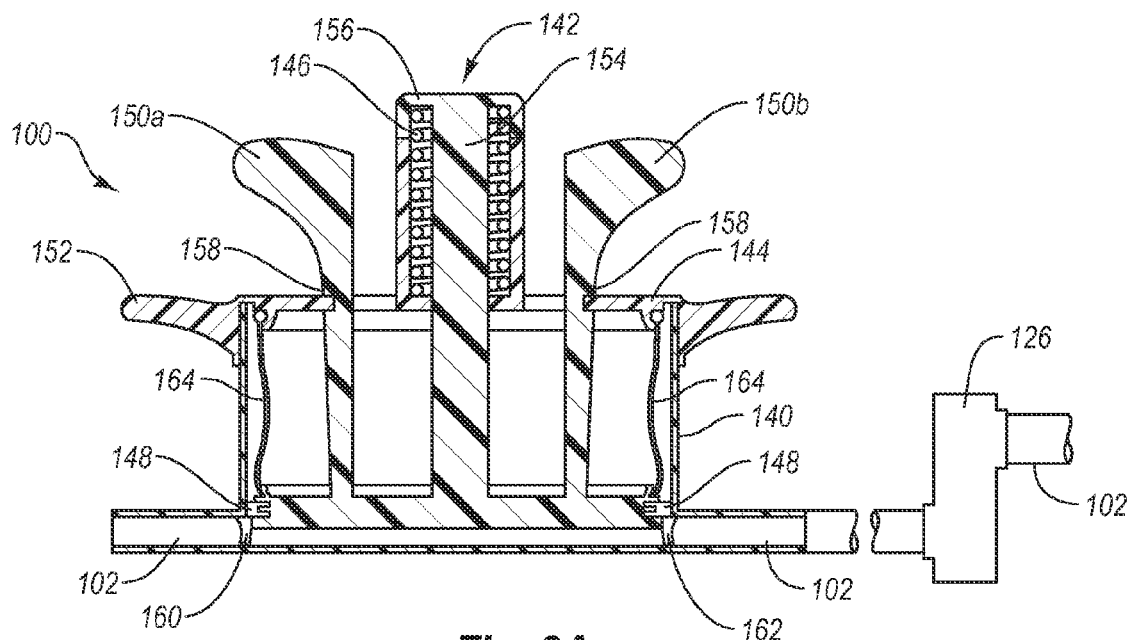
FIG. 2A illustrates a cross-sectional view of a fluid drawing device according to one embodiment of the present invention.

Embodiments of the present invention described herein relate to a fluid sampling system. The fluid sampling system can include a fluid drawing device, a fluid sampling device, and a modified glucometer to accommodate the fluid sampling device. Other standard medical equipment used in conjunction with these elements can include a pressure transducer, an IV stand, a pressure bag, saline solution, IV tubing, and a peripheral IV, an Arterial Line or a Central Venous Line, for example.

The fluid drawing device of the fluid sampling system can be used to draw bodily fluid, such as blood, from a patient injection site into an IV tube or catheter. After the fluid has been drawn into the IV tube, the fluid sampling device can be introduced into a sample port of the IV tube to retrieve a sample of the bodily fluid. After a fluid sample has been retrieved, the fluid sample can be analyzed with a glucometer that can be modified to accommodate the fluid sampling device. The fluid sampling system of the present invention can provide a safe method of obtaining a sample of bodily fluid from a patient. For instance, the fluid sampling system can reduce the need to use needles each time a blood sample is needed, which in turn can reduce the pain and discomfort a patient experiences each time he or she is pricked. Further, the possibility that a health care worker will be pricked with a contaminated needle can be reduced with use of the fluid sampling system. Additionally, the fluid sampling system can be simple to use, thus allowing health care workers to focus on other aspects of the patient's treatment.

In the disclosure, reference is made to the use of a test strip with a fluid sampling device. As used in the disclosure and the claims, a test strip can be any device capable of detecting attributes of a fluid sample. For example, a test strip can comprise a substrate with an absorbent material and a reagent disposed thereon. Alternatively, a test strip can comprise electrical leads or connections which can communicate various properties of a fluid sample to an analysis device, such as a glucometer. It will be appreciated that a test strip can also comprise a combination of any one or more of a reagent, an absorbent material, and electrical connections. While some embodiments herein are described with reference to a specific type of test strip, it will be appreciated that the specific test strip described in each embodiment can be interchanged or replaced with another type of test strip. For example, a test strip having an absorbent material and/or a reagent can be replaced with a test strip having electrical connections.

In one example embodiment, an IV tube is connected to a pressure bag (or a pressure transducer) at one end thereof, while the other end of the IV tube is in fluid communication with a patient injection site. Unlike typical IV systems, the present example embodiments also have a fluid drawing device connected to the IV tube between the pressure bag and the patient such that fluid flowing through the IV tube also flows through the fluid drawing device. In addition, the IV tube also includes a sample port between the fluid drawing device and the patient. The fluid sampling device can be inserted into the sample port in order to take a sample of the fluid in the IV tube.

When the fluid sampling system is configured as described above, a user, such as a doctor or nurse, can take a sample of a patient's bodily fluid, such as blood, by activating the fluid drawing device, which draws the bodily fluid into the IV tube past the sample port, allowing the user to access the bodily fluid at the sample port with the fluid sampling device. The fluid drawing device has a fill chamber through which the fluid from the IV tube can flow. Disposed within the fill chamber is a plunger that can be positioned between a first position and a second position. The plunger can be locked in the first and/or the second positions. To activate the fluid drawing device, the user releases the locking mechanism on the plunger. Once the plunger is unlocked, the plunger can move toward the second position, thus creating a negative pressure in the IV tube, which draws the bodily fluid into the IV tube past the sample port. The user can then insert the fluid sampling device into the sample port to retrieve a sample of the bodily fluid. When a sufficient fluid sample has been retrieved, the fluid sampling device can be removed from the sample port and the user can depress the plunger of the fluid drawing device to force the extra bodily fluid back into the patient. The fluid sampling device can be configured to have a test strip disposed therein. When the bodily fluid enters the fluid sampling device from the sample port, the bodily fluid can be absorbed by the test strip. The sample of bodily fluid absorbed by the test strip can then be analyzed by a glucometer.

As seen in FIG. 1, an exemplary embodiment of the fluid sampling system 50 can include an IV tube 102, a fluid drawing device 100, a sample port 126, and a fluid sampling device 200 and/or 400. Fluid drawing device 100 is in fluid communication with IV tube 102 such that fluid drawing device 100 can draw fluid through IV tube 102 past sample port 126. After fluid drawing device 100 has drawn fluid past sample port 126, fluid sampling device 200 or 400 can be introduced into sample port 126 to obtain a fluid sample.

Figure 2B:
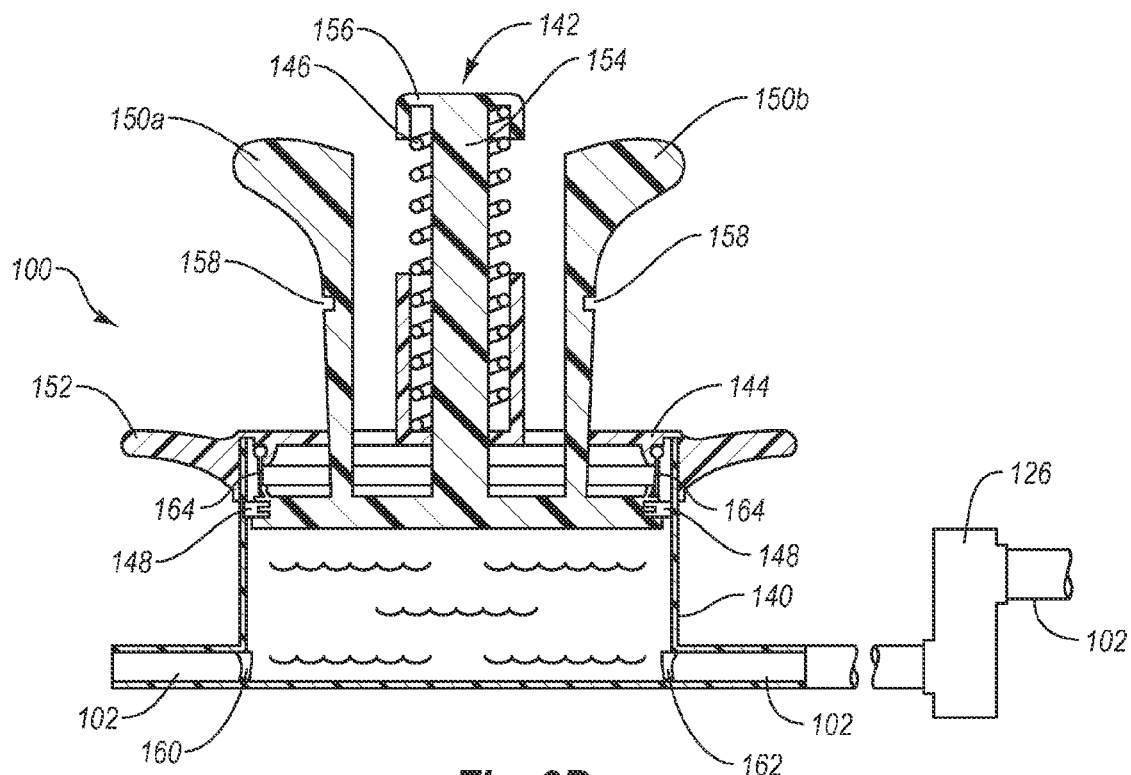
FIG. 2B illustrates a cross-sectional view of the fluid drawing device of FIG. 2A after the fluid drawing device has been activated.

FIGS. 2A-2B illustrate an exemplary embodiment of fluid drawing device 100. In this embodiment, fluid drawing device 100 comprises a housing 140, a piston 142 partially disposed within housing 140, locking mechanism 150 connected to piston 142, a cap 144 coupled to the top of housing 140, and a spring 146. Housing 140 of fluid drawing device 100 is in fluid communication with IV tube 102 such that fluid flowing through IV tube 102 flows from a first portion of IV tube 102 through housing 140 and into a second portion of IV tube 102. At the point of connection between the first portion of IV tube 102 and housing 140 there is a first valve 160. First valve 160 is a one-way valve that allows fluid to flow from the first portion of IV tube 102 into housing 140. At the point of connection between housing 140 and the second portion of IV tube 102 there is a second valve 162. Second valve 162 is configured to allow fluid to flow both into and out of housing 140. The direction of fluid flow through second valve 162 is determined by the pressure in the system. In alternative embodiments, one or both of first and second valves 160 and 162 are not incorporated into the system. IV tube 102 and valves 160 and 162 can be made of a medical grade plastic and/or rubber.

Cap 144 connects to the top portion of housing 140. Extending out from cap 144 are cap handles 152. Cap handles 152 are sized and shaped to assist a user in compressing piston 142 into its first position, as seen in FIG. 2A. Cap 144 has at least one opening therein to allow portions of piston 142 and locking mechanism 150 to extend therethrough. Cap 144 is configured to restrict the movement of piston 142 such that the first end of piston 142 remains within housing 140. Coupled to a bottom surface of cap 144 is a sterility liner 164. Sterility liner 164 also couples to piston 142 (described below). Sterility liner 164 can be coupled to cap 144 and piston 142 by any suitable means, such as clamps, O-rings, glue, and the like. Sterility liner 164 functions to prevent the interior of housing 140 from becoming contaminated. When piston 142 is in the position illustrated in FIG. 2A, a portion of the interior of housing 140 is exposed. To prevent the interior walls of housing 140 from becoming contaminated, sterility liner 164 is used to enclose at least a portion of the interior of housing 140 so as to prevent contamination of the interior walls of housing 140. Without sterility liner 164, housing 140 could become contaminated, which contamination would enter the fluid sampling system when piston 142 is moved to the position illustrated in FIG. 2B. Such contamination could expose a risk to a patient. Sterility liner 164 can be made of an air-impermeable material, such as a film of plastic.

A first end of piston 142 is slidably disposed within housing 140. Extending around the edge of the first end of piston 142 is a seal 148. Seal 148 abuts the interior wall of housing 140, creating an airtight seal between piston 142 and housing 140 such that movement of piston 142 within housing 140 causes an increase or decrease in pressure within housing 140. Seal 148 can be an integral part of piston 142 or it can be a distinct piece adapted to be coupled to the first end of piston 142. Seal 148 can be made of a medical grade plastic and/or rubber.

Piston 142 has a rod 154 that extends from the first end of piston 142 and through cap 144. Spring 146 is concentrically placed around rod 154. The first end of spring 146 rests on the top of cap 144. Rod 154 has a rim 156 that extends over the second end of spring 146, thus retaining spring 146 between cap 144 and rim 156. When piston 142 is moved from a second position (shown in FIG. 2B) to the first position shown in Figure 2A, spring 146 is compressed between rim 156 and cap 144. Spring 146 therefore biases piston 142 toward the second position shown in FIG. 2B relative to the first position shown in FIG. 2A.

In addition to rod 154, extending from the first end of piston 142 is locking mechanism 150. In the example embodiment, locking mechanism 150 comprises two levers 150a, 150b that extend from opposing sides of the first end of piston 142 through cap 144. Levers 150a and 150b are biased toward housing 140. Each of levers 150a and 150b has a notch 158 in an outer surface thereof that is sized and shaped to engage cap 144, thus preventing movement of piston 142 relative to housing 140. Levers 150a and 150b can be compressed toward rod 154 to disengage notches 158 from cap 144, thus allowing piston 142 to move relative to housing 140. When cap 144 engages notches 158, piston 142 is held in the position shown in FIG. 2A. As can be seen, even when spring 146 is compressed and locking mechanism 150 is preventing movement of piston 142, there is sufficient space between housing 140 and the first end of piston 142 to allow fluid to flow therethrough.

In use, fluid drawing device 100 is connected to IV tube 102 and piston 142 is locked in the down position illustrated in FIG. 2A. To draw fluid using the present exemplary embodiment of fluid drawing device 100, a user activates fluid drawing device 100 by compressing levers 150a and 150b to disengage piston 142 from housing 140. When piston 142 is disengaged from housing 140, spring 146 biases piston 142 upward to the position illustrated in FIG. 2B. As piston 142 moves upward within housing 140, a negative pressure is created in housing 140 causing first valve 160 to close, preventing fluid from flowing from the first portion of IV tube 102 into housing 140. The negative pressure created in housing 140 when piston 142 moves upward draws the fluid in the second portion of IV tube 102 back into housing 140. Spring 146 is designed to have sufficient travel and force to provide the necessary displacement to draw fluid, such as blood, from a patient into the second portion of IV tube 102. As the fluid in the second portion of IV tube 102 is drawn back into housing 140, a negative pressure is created in the second portion of IV tube 102, which in turn draws fluid from the patient's body back into the second portion of IV tube 102 past sample port 126. After the bodily fluid has been drawn past sample port 126, the user can then insert the fluid sampling device (described in detail below) into sample port 126 to retrieve the desired fluid sample. The negative pressure in housing 140 does not exceed that which is produced during regular phlebotomy by commonly used vacuum packed test tubes. After the fluid sample has been retrieved, the user can return the system to its original configuration (as seen in FIG. 2A) by pressing piston 142 back to its original position which re-infuses the patient's fluid into their body. When piston 142 is depressed, locking mechanism 150 can be re-engaged and fluid flow through the system can be restored to its original rate.

The various components of the fluid drawing device can be made from a medical device industry standard, including, but not limited to thermoplastics, such as Polyethylene (PE), High Density Polyethylene (HDPE), Polypropylene (PP), Polystyrene (PF), Polyethylene Terephthalate (PET), and acrylic (for elements that are desired to be transparent, such as chambers 106, 110 and housing 140, for example), because of their low cost production, ability to be easily molded, sterility, and strength. Spring 146 can be made of steel or any other resilient metal or plastic material. It will be understood by one of ordinary skill in the art in view of the disclosure provided herein that spring 146 can be a flexible member used to store mechanical energy.

Figure 3:
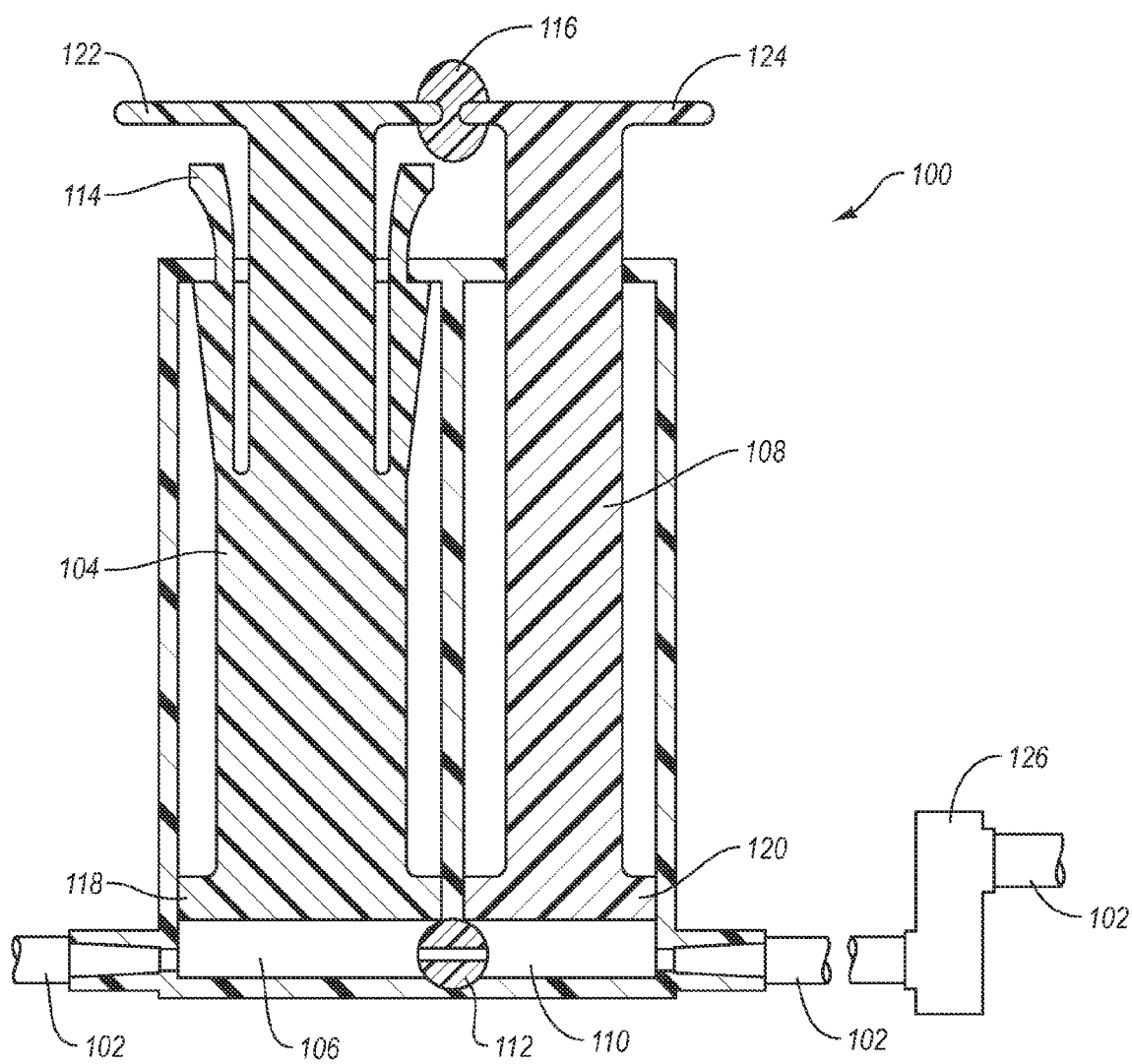
FIG. 3 illustrates a cross-sectional view of an alternate example embodiment of a fluid drawing device of the present invention.
Figure 5A:
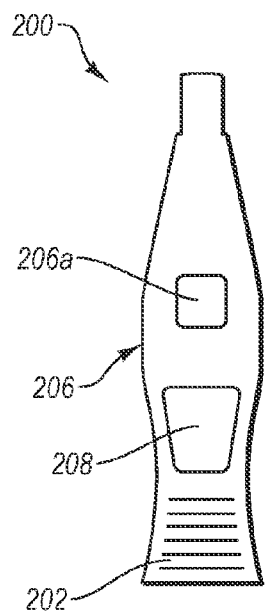
FIG. 5A illustrates a top view of an alternative embodiment of the fluid sampling device of the present invention.
Figure 5B:
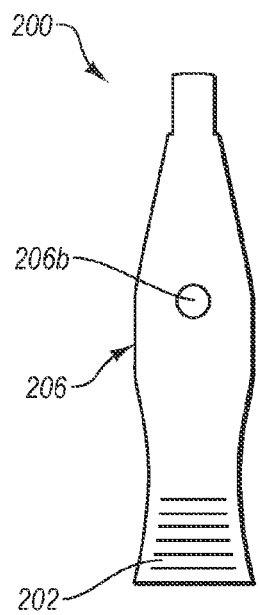
FIG. 5B illustrates a bottom view of the alternative embodiment of the fluid sampling device of FIG. 5A.
Figure 5C:
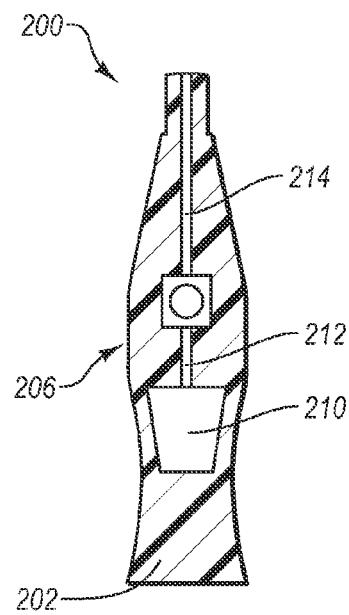
FIG. 5C illustrates a cross-sectional view of the alternative embodiment of the fluid sampling device of FIG. 5A.
Figure 5D:
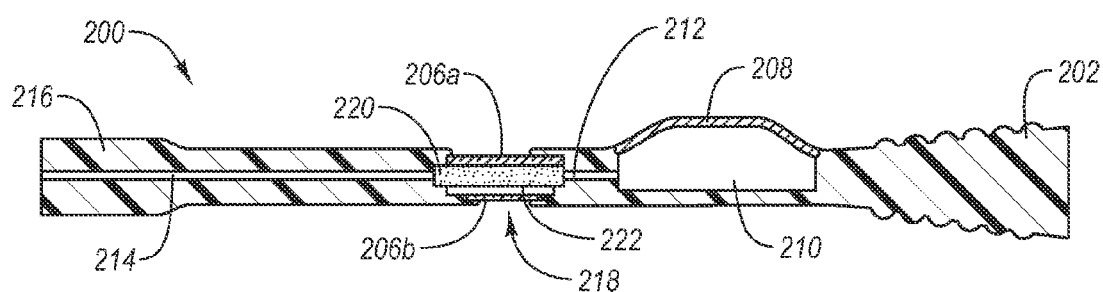
FIG. 5D illustrates a cross-sectional side view of the alternative embodiment of the fluid sampling device of FIG. 5A.

FIG. 3 illustrates an alternative exemplary embodiment of the fluid drawing device 100. The fluid drawing device 100 comprises a driver plunger 104, the first end of which is disposed within a driver chamber 106. The first end of driver plunger 104 has a driver ridge 118 that sealingly engages the interior wall of driver chamber 106. Driver ridge 118 can be an integral part of driver plunger 104 or it can be a distinct piece adapted to couple to the first end of driver plunger 104. In either configuration, driver ridge 118 is adapted to create an airtight seal between driver plunger 104 and driver chamber 106 such that movement of driver plunger 104 within driver chamber 106 causes a corresponding change in pressure within driver chamber 106. Driver ridge 118 can be made of a medical grade plastic or rubber.

The second end of driver plunger 104 comprises a driver handle 122 which extends outside of driver chamber 106. The second end of driver plunger 104 also has a locking mechanism 114 disposed thereon. Locking mechanism 114 comprises at least one leaf spring type structure that extends away from a side of driver plunger 104 and that can engage an interior surface of driver chamber 106 to prevent driver plunger 104 from moving relative to driver chamber 106. Locking mechanism 114 can be compressed to disengage driver plunger 104 from driver chamber 106, thus allowing driver plunger 104 to move relative to driver chamber 106. When locking mechanism 114 is engaged with driver chamber 106, a space between the bottom of driver chamber 106 and the bottom surface of driver plunger 104 is created that is sufficient to allow fluid to flow therethrough.

Fluid drawing device 100 also has a fluid fill plunger 108, the first end of which is disposed within a fluid fill chamber 110. The first end of fluid fill plunger 108 has a ridge 120 that sealingly engages the interior wall of fluid fill chamber 110. Ridge 120 can be an integral part of fluid fill plunger 108 or it can be a distinct piece adapted to couple to the first end of fluid fill plunger 108. In either configuration, ridge 120 is adapted to create an airtight seal between fluid fill plunger 108 and fluid fill chamber 110 such that movement of fluid fill plunger 108 within fluid fill chamber 110 causes a corresponding change in pressure within fluid fill chamber 110. Ridge 120 can be made of a medical grade plastic or rubber.

The second end of fluid fill plunger 108 comprises a fluid fill plunger handle 124 which extends outside of fluid fill chamber 110. Driver plunger handle 122 and fluid fill plunger handle 124 can be connected with connector lock 116 so that the movement of driver plunger 104 and fluid fill plunger 108 is connected. When locking mechanism 114 is engaged with driver chamber 106, thus restricting movement of fluid fill plunger 108 through connector lock 116, a space between the bottom of fluid fill chamber 110 and the bottom surface of fluid fill plunger 108 is created that is sufficient to allow fluid to flow therethrough.

Driver chamber 106 and fluid fill chamber 110 are in fluid communication with each other and with IV tube 102. As can be seen in FIG. 3, a fluid in IV tube 102 can flow through driver chamber 106, into fluid fill chamber 110, and on into a second portion of IV tube 102. The second portion of IV tube 102 has a sample port 126 into which a user may insert a fluid sampling device 200 or 400 to retrieve a fluid sample, such as a blood sample. As the fluid flows from driver chamber 106 to fluid fill chamber 110, it passes through flow gauge 112. Flow gauge 112 is a valve that regulates the amount of fluid that can pass from driver chamber 106 to fluid fill chamber 110, and thus into the patient. Flow gauge 112 can be adjusted by a user to allow a desired amount of fluid to pass from driver chamber 106 to fluid fill chamber 110. In the example embodiment, flow gauge 112 is configured to allow about 3 cc/hr to flow from driver chamber 104 to fluid fill chamber 110. Flow gauge 112 also acts as a one-way valve to prevent fluid from flowing from fluid fill chamber 110 to driver chamber 106.

As noted above, fluid drawing device 100 can be connected in line with IV tube 102 which can be used for delivering a fluid, such as saline and/or a medicament to a patient. While fluid is being delivered to a patient through IV tube 102, driver plunger 104 and fluid fill plunger 108 of fluid drawing device 100 are in the positions illustrated in FIG. 3. To retrieve a sample of bodily fluid using fluid drawing device 100, a user activates fluid drawing device 100 by compressing locking mechanism 114 which disengages driver plunger 104 from driver chamber 106. The fluid pressure in IV tube 102 causes driver plunger 104 to move up in driver chamber 106. Upward movement of driver plunger 104 reduces the pressure in driver chamber 106 causing flow gauge 112 to close, preventing fluid from flowing from driver chamber 106 to fluid fill chamber 110. Connector lock 116 causes fluid fill plunger 108 to move up simultaneously with driver plunger 104. As fluid fill plunger 108 moves up in fluid fill chamber 110, a negative pressure is created in fluid fill chamber 110 which draws the fluid in the second portion of IV tube 102 back into fluid fill chamber 110. As the fluid in the second portion of IV tube 102 is drawn back into fluid fill chamber 110, a negative pressure is created in the second portion of IV tube 102, which in turn draws a bodily fluid, such as blood, from the patient back into the second portion of IV tube 102 past sample port 126.

After the bodily fluid has been drawn into IV tube 102, the user can then insert fluid sampling device 200 or 400 (described in detail below) to retrieve the desired fluid sample. The negative pressure in fluid fill chamber 110 does not exceed that which is produced during regular phlebotomy by commonly used vacuum packed test tubes. Once the desired fluid sample is retrieved, fluid sampling device 200 or 400 can be removed from sample port 126. The user can then return the system to its original configuration by pressing fluid fill plunger 108 back to its original position which re-infuses the patient's bodily fluid into their body. The user can then press the driver plunger 104 back to its original position and re-engage locking mechanism 114. Once both plungers 104 and 108 are depressed, flow gauge 112 opens and allows the system to deliver the desired amount of fluid to the patient.

FIGS. 4A and 4B illustrate an exemplary embodiment of the fluid sampling device 200. Fluid sampling device 200 comprises a handle 202, a blunt cannula 204, and a main body 206 having an interior portion and windows 206a and 206b. Blunt cannula 204 is sized and shaped to fit within sample port 126 (see FIG. 1). Blunt cannula 204 has an opening in an end thereof that is in fluid communication with the interior portion of main body 206. The interior portion of main body 206 is adapted to hold a fluid sample, such as a blood sample. Windows 206a and 206b are disposed on opposing sides of main body 206 and allow a user to view the interior portion of main body 206. Windows 206a and 206b also facilitate analysis of the fluid sample when analyzed by a modified glucometer, as discussed below. Handle 202 is ergonomically shaped to allow a user to easily and comfortably hold fluid sampling device 200 with a thumb and forefinger.

In use, after fluid drawing device 100 has been activated and a fluid has been drawn past sample port 126, blunt cannula 204 can be inserted into sample port 126. A small volume of fluid can be drawn through the blunt cannula into the interior portion of main body 206 by pressure, such as hydrostatic, hemodynamic, and/or mechanically induced pressure. Windows 206a and 206b enable a user to view the fluid sample and determine when a sufficient sample has been obtained. Fluid sampling device 200 can then be removed from sample port 126 and the fluid sample can be analyzed by a modified glucometer, as discussed below.

FIGS. 5A-5D illustrate an alternative exemplary embodiment of fluid sampling device 200. Similar to the previous embodiment, fluid sampling device 200 comprises a handle 202, a main body 206, and windows 206a and 206b. In addition, fluid sampling device 200 of the present embodiment comprises a diaphragm 208, a vacuum chamber 210 disposed within main body 206, a first channel 212, a second channel 214, a luer lock tip 216, and a testing compartment 218 disposed within main body 206.

As seen in the Figures, adjacent handle 202, and disposed within main body 206, is a vacuum chamber 210. Vacuum chamber 210 is defined by main body 206 and diaphragm 208. Diaphragm 208 is generally arch shaped and is made from a resilient, pliable material, such as rubber or plastic, so that a user can depress diaphragm 208 to decrease the volume of vacuum chamber 210. Vacuum chamber 210 is in fluid communication with first channel 212 such that when diaphragm 208 is depressed, air from vacuum chamber 210 is expelled through first channel 212. First channel 212 extends from vacuum chamber 210 to testing compartment 218.

Testing compartment 218 is disposed within main body 206 and is partially defined by windows 206a and 206b which are on opposing sides of main body 206. Windows 206a and 206b allow a user to view the interior of testing compartment 218 and determine when a sufficient sample of fluid has been obtained. Within testing compartment 218 is an absorbent material 220, such as foam, and a testing reagent 222. Absorbent material 220 absorbs and retains a fluid sample that is retrieved from sample port 126 as described below. Testing reagent 222 is disposed adjacent absorbent material 220 such that absorbed fluid will contact testing reagent 222. Testing reagent 222 will react to various attributes of the fluid sample, such as glucose levels of a blood sample.

Testing compartment 218 is in fluid communication with second channel 214. Second channel 214 extends through luer lock tip 216 and opens at the end of luer lock tip 216. Luer lock tip 216 can be retrofitted with a blunt cannula in order to access various applicable systems, such as sample port 126.

Fluid sampling device 200 of the present embodiment is used in a manner similar to fluid sampling device 200 of the previous embodiment. When fluid drawing device 100 has been activated and a fluid has been drawn into IV tube 102 past sample port 126, fluid sampling device 200 can be used to retrieve a fluid sample from sample port 126. The present example embodiment of fluid sampling device 200 does not rely on hydrostatic or hemodynamic pressure to draw fluid from sample port 126 into fluid sampling device 200. Rather, the present embodiment of fluid sampling device 200 utilizes a negative pressure within vacuum chamber 210 to draw fluid from sample port 126 into fluid sampling device 200. Specifically, prior to inserting luer lock tip 216 into sample port 126, a user will depress diaphragm 208 to expel air out of vacuum chamber 210 through first channel 212, testing compartment 218, and second channel 214, thus creating a potential vacuum within vacuum chamber 210. Once the potential vacuum has been created in vacuum chamber 210, luer lock tip 216, either as shown in the FIGS. 5A-5D or retrofitted with a blunt cannula, is inserted into sample port 126 (see FIG. 1). The user then releases diaphragm 208 to return to its original shape and position. As diaphragm 208 returns to its original position, a negative pressure or vacuum is created within vacuum chamber 210. Vacuum chamber 210 and diaphragm 208 are sized and adapted to create a negative pressure within fluid sampling device 200 sufficient to draw a desired quantity of fluid from sample port 126, through second channel 214, and into testing compartment 218

As the fluid enters testing compartment 218, absorbent material 220 will absorb the fluid and distribute it across testing reagent 222. Absorbent material 220 also functions to retain fluid within fluid sampling device 200. Windows 206a and 206b allow a user to view absorbent material 220 in testing compartment 218 to determine when an adequate fluid sample has been achieved. When a sufficient quantity of fluid has been drawn into testing compartment 218, the user removes fluid sampling device 200 from sample port 126.

Figure 7:
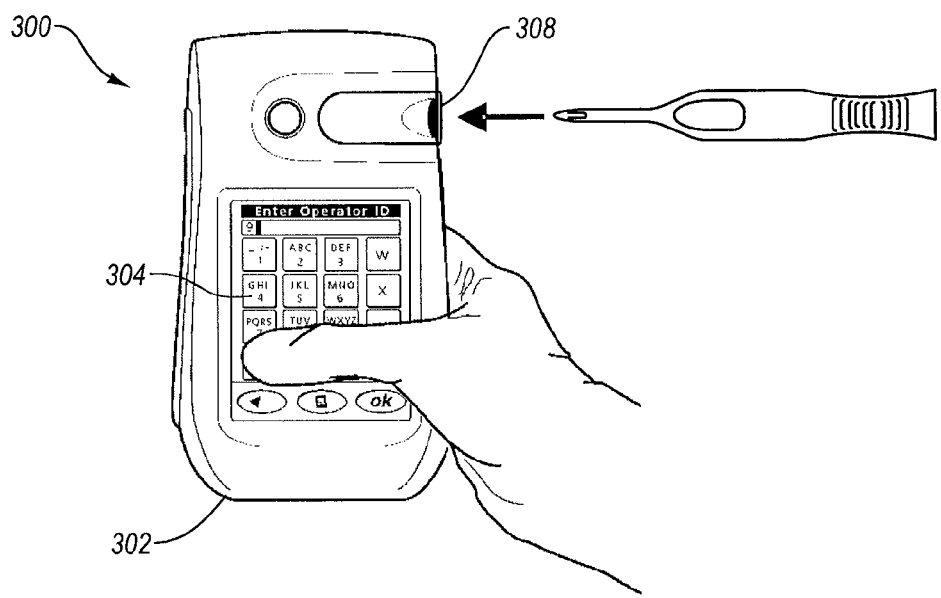
FIG. 7 illustrates a modified glucometer according to one embodiment of the present invention.

Having obtained a fluid sample within fluid sampling device 200, the fluid sample can then be analyzed using a modified glucometer 300 as seen in FIG. 7. Glucometers are well known in the art. A typical glucometer 300 comprises a housing 302, a keypad 304, internal analysis apparatus 306 (not shown), and a receptacle 308 for receiving a test strip having a fluid sample, such as a blood sample, disposed thereon. The modified glucometer shown in FIG. 7 has a reconfigured receptacle 308 that is designed to receive fluid sampling device 200 therein. Receptacle 308 is adapted such that when fluid sampling device 200 is inserted therein, windows 206a and 206b are in alignment with an analyzer light (not shown) of modified glucometer 300. The analyzer light of modified glucometer 300 is directed through one or both of windows 206a and 206b to analyze various attributes of the fluid sample, such as glucose levels of a blood sample.

Figure 6:
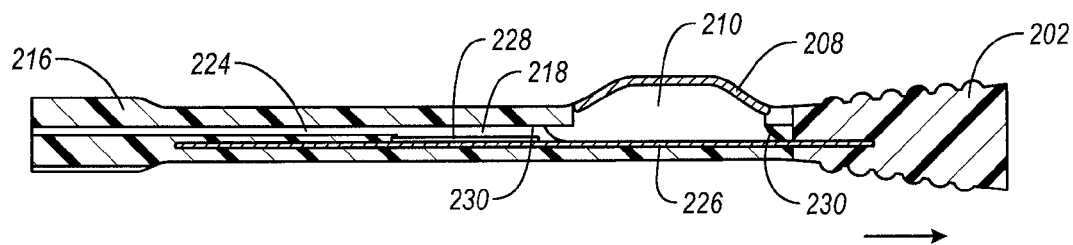
FIG. 6 illustrates a cross-sectional side view of another alternative embodiment of the fluid sampling device of FIG. 5A.

FIG. 6 illustrates yet another exemplary embodiment of fluid sampling device 200. Fluid sampling device 200 of the present embodiment comprises handle 202, vacuum chamber 210, diaphragm 208, testing compartment 218, luer lock tip 216, channel 224, test strip 226, reagent 228, and valves 230. Vacuum chamber 210 is in fluid communication with channel 224 to allow air to be expelled from vacuum chamber 210 through channel 224 when diaphragm 208 is depressed. Expulsion of air from vacuum chamber 210 creates a potential vacuum therein.

Fluid sampling device 200 is adapted to receive a standard test strip 226 disposed at least partially therein. In the illustrated embodiment, test strip 226 is received within testing compartment 218, vacuum chamber 210 and handle 202. Fluid sampling device 200 can be adapted to receive standard supply test strips such as the SureStep Pro™ glucose test strip made by LifeScan® (a Johnson & Johnson subsidiary).

Fluid sampling device 200 of the present embodiment is used in a manner similar to the previous embodiments of fluid sampling device 200 equipped with diaphragm 208. Specifically, a user depresses diaphragm 208 to expel air out of vacuum chamber 210 and create a potential vacuum therein. Lure lock tip 216, either as illustrated or retrofitted with a blunt cannula, is inserted into sample port 126 and diaphragm 208 is released to create a negative pressure within vacuum chamber 210. The negative pressure within vacuum chamber 210 draws fluid from sample port 126 through channel 224 into testing compartment 218. Fluid entering testing compartment 218 is absorbed by test strip 226. Having received a sufficient fluid sample, fluid sampling device 200 can be removed from sample port 126.

As seen in FIG. 6, unlike the previous embodiments of fluid sampling device 200, handle 200 of the present embodiment can be removed to expose an end of test strip 226. Handle 200 can be coupled to fluid sampling device 200 with the use of clamps, clips, or the like. With handle 202 detached from fluid sampling device 200, test strip 226 can be removed from fluid sampling device 200 for analysis of the fluid sample. By adapting fluid sampling device 200 with a removable handle 202, the fluid sample disposed on test strip 226 can be analyzed using conventional means, such as a typical glucometer that is adapted to receive standard test strips. To prevent potential air leaks through handle 202 that would reduce the drawing force of vacuum chamber 210 and diaphragm 208, fluid sampling device 200 has one-way valve 230 disposed across the opening through which test strip 226 is inserted.

Figure 8:
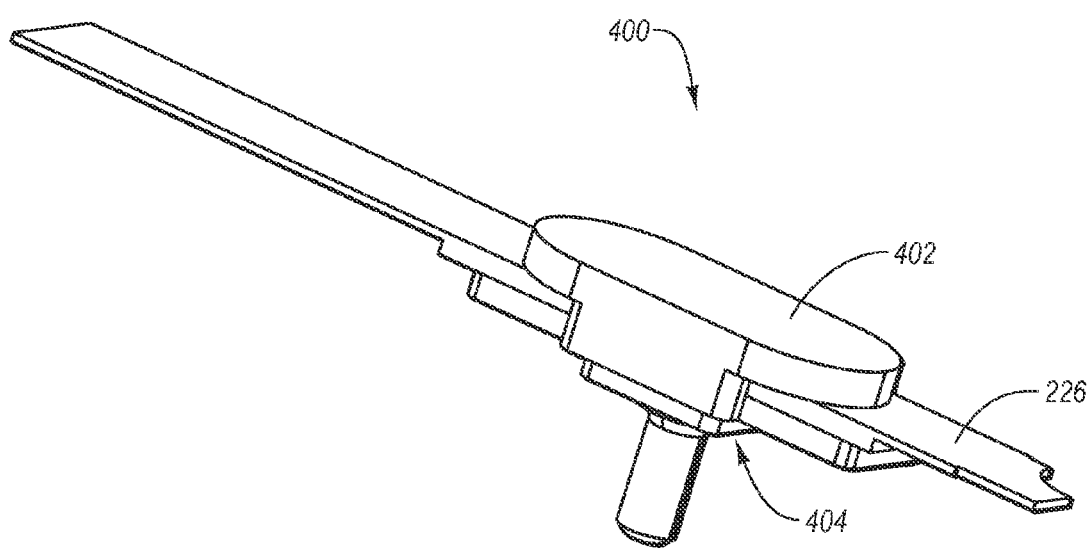
FIG. 8 illustrates a perspective view of a fluid sampling device according to another embodiment of the present invention.
Figure 11:
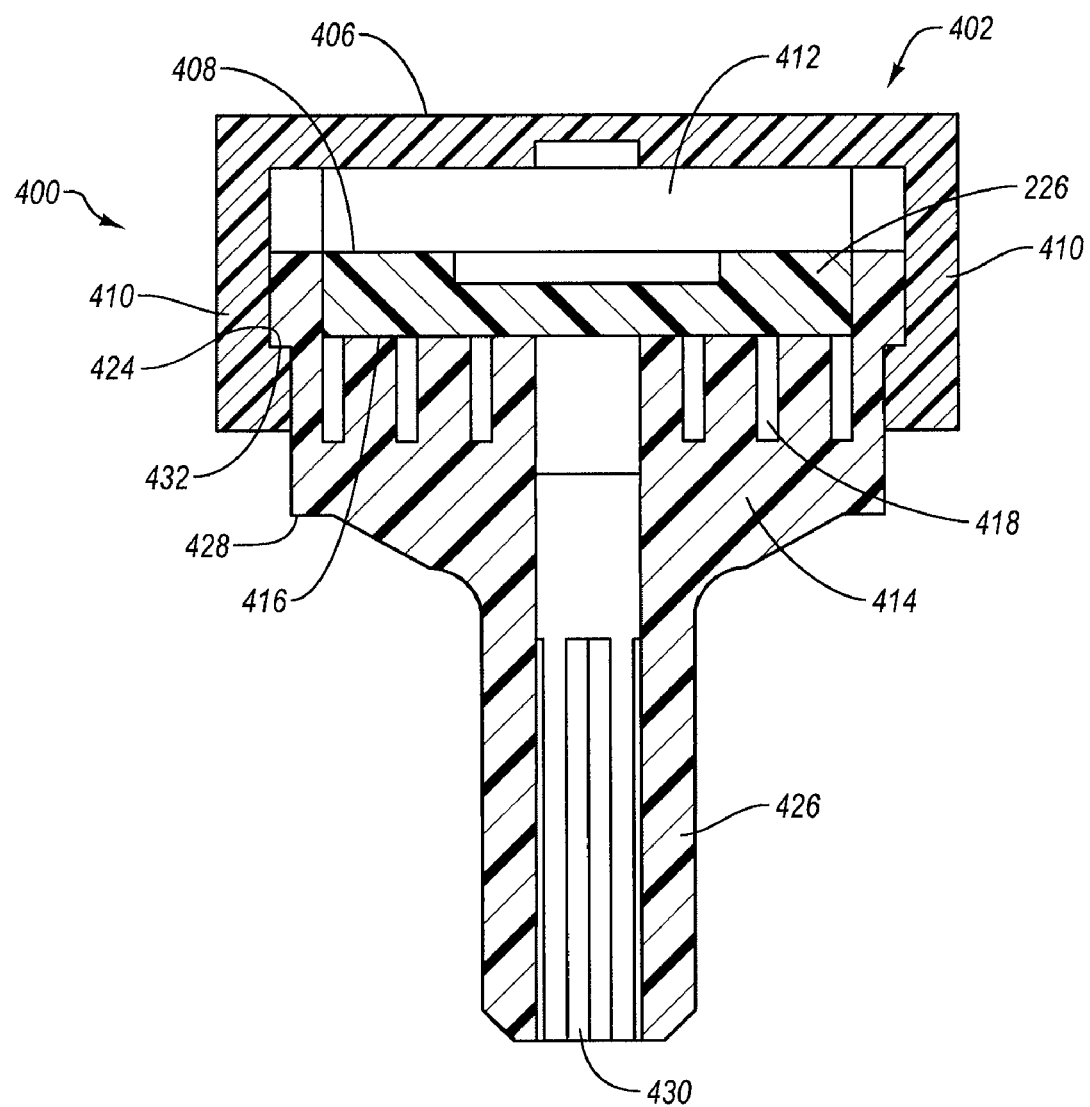
FIG. 11 illustrates a cross-sectional end view of the fluid sampling device of FIG. 8.

FIG. 8 illustrates a perspective view of yet another embodiment of fluid sampling device 400. Fluid sampling device 400 of the present embodiment comprises a top portion 402 and a base portion 404 that are adapted to be coupled together. Top portion 402 and base portion 404 can be coupled together in a first position and a second position. In the first position, fluid sampling device 400 can have a test strip 226 disposed between base portion 404 and top portion 402 (as seen in FIGS. 8 and 11). It is contemplated that standard test strips, such as the SureStep Pro™ glucose test strip made by LifeScan® (a Johnson & Johnson subsidiary) can be used in combination with fluid sampling device 400. Top portion 402 is biased toward base portion 404 such that when test strip 226 is removed top portion 402 moves toward base portion 404. Fluid sampling device 400 can be configured for insertion within sample port 126 to obtain a fluid sample as illustrated in FIG. 1. In an alternative embodiment, top portion 402 can comprise test strip 226. In this embodiment, base portion 404 and test strip 226 can be coupled together with a flange, an adhesive such as glue, or a mechanical fastener.

Figure 9A:
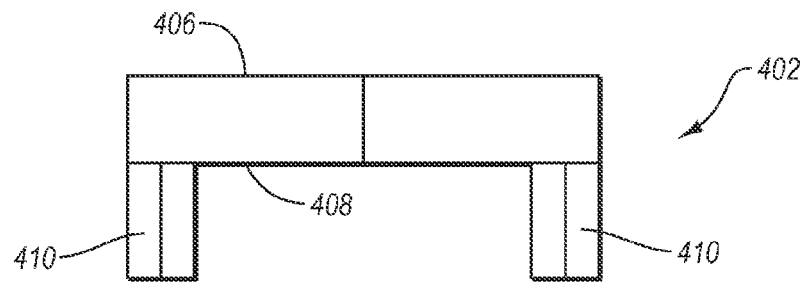
FIG. 9A illustrates an end view of the top portion of the fluid sampling device of FIG. 8.
Figure 9B:
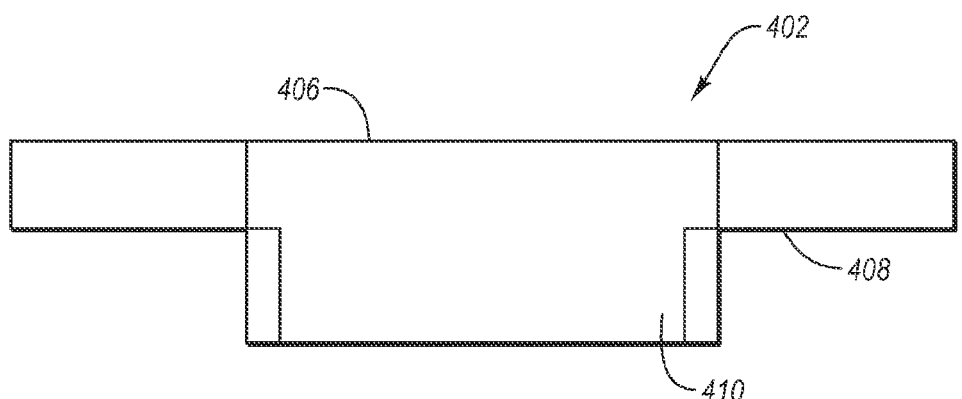
FIG. 9B illustrates a side view of the top portion of the fluid sampling device of FIG. 8.
Figure 9C:
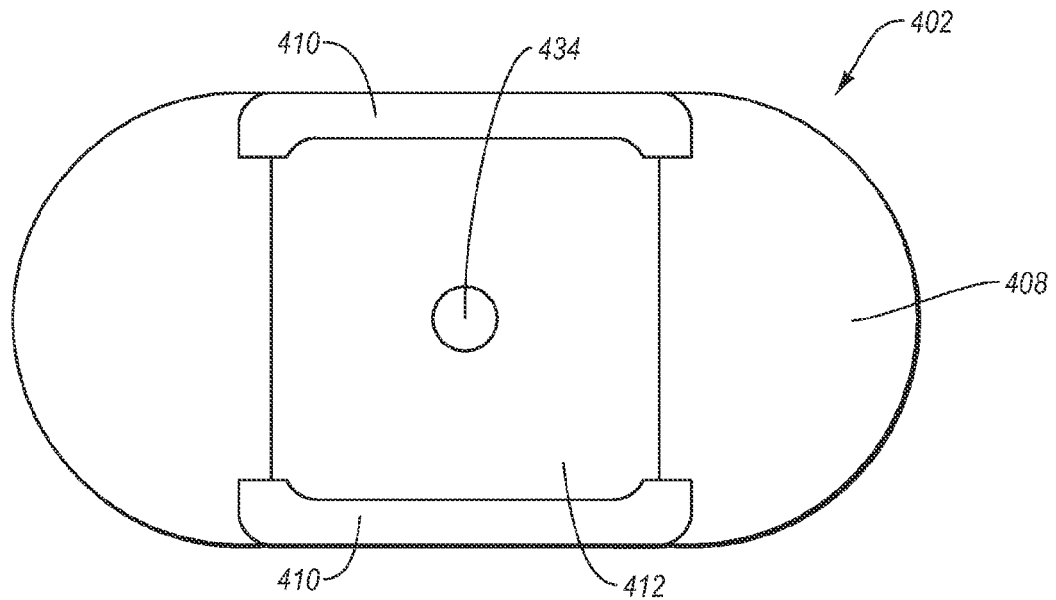
FIG. 9C illustrates a bottom view of the top portion of the fluid sampling device of FIG. 8.

FIGS. 9A-9C illustrate end, side, and bottom views of top portion 402. As seen in the Figures, top portion 402 comprises a top surface 406, a bottom surface 408, flanges 410, and recess 412. Top surface 402 defines an aperture 434 that can allow a user to view the interior of fluid sampling device 400 to determine when a sufficient fluid sample had been obtained. Flanges 410 are disposed on opposing sides of top portion 402 and extend from bottom surface 408. The ends of flanges 410 are rounded in toward the center of top portion 402. Recess 412 is a cavity in bottom surface 408. The various elements of top portion 402 can be integrally formed as a unitary piece, or the elements can be individually formed and then coupled together. As noted above, top portion 402 can comprise test strip 226.

Figure 10A:
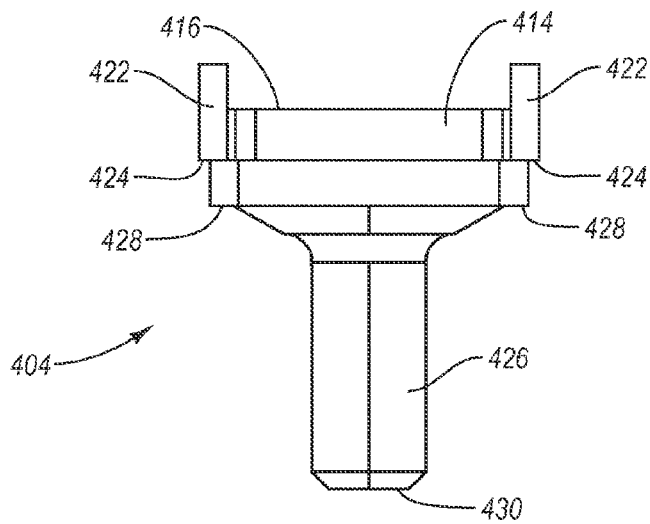
FIG. 10A illustrates an end view of the base portion of the fluid sampling device of FIG. 8.
Figure 10B:
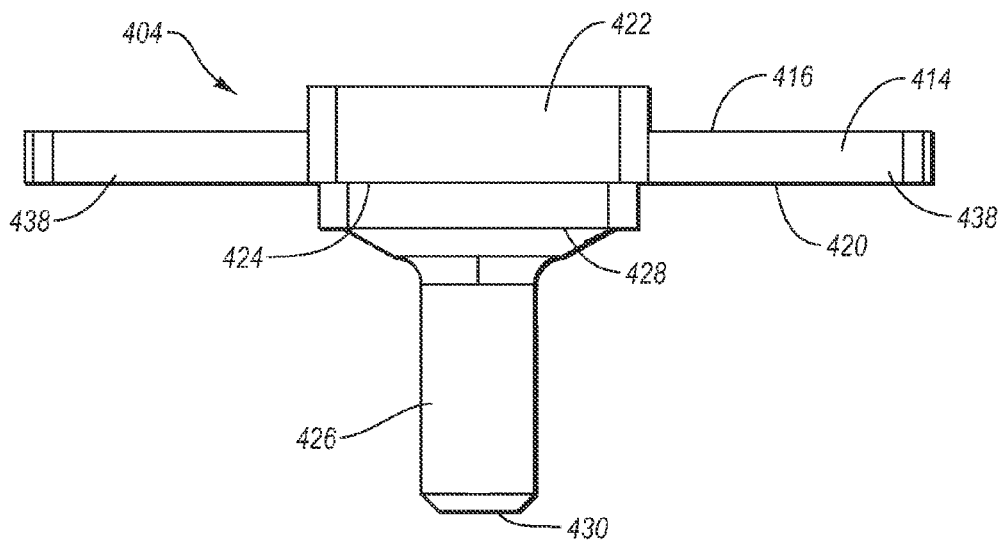
FIG. 10B illustrates a side view of the base portion of the fluid sampling device of FIG. 8.
Figure 10C:
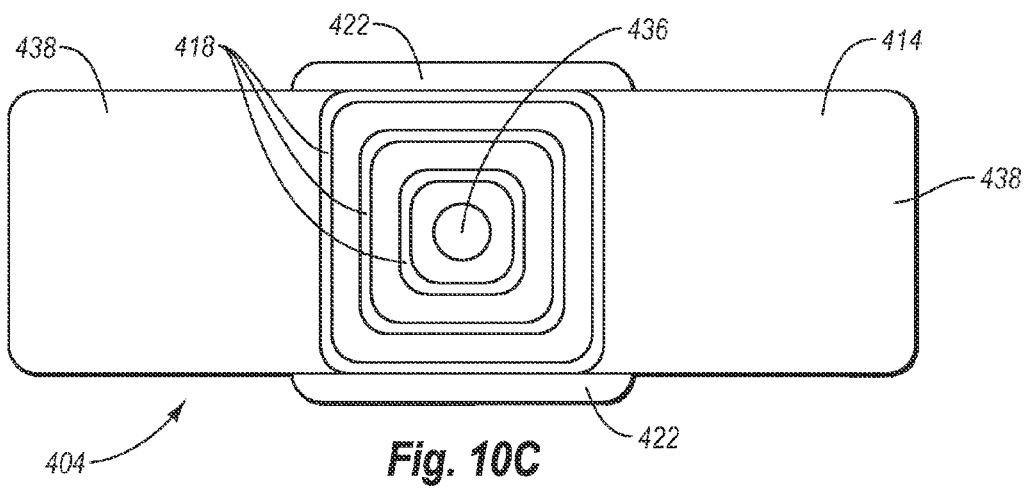
FIG. 10C illustrates a top view of the base portion of the fluid sampling device of FIG. 8.

FIGS. 10A-10C illustrate end, side, and bottom views of base portion 404. Base portion 404 comprises a platfoim 414, walls 422, and a blunt cannula 426. Platform 414 has a bottom surface 420 and a top surface 416 with grooves 418 therein as seen in FIG. 10C. The opposing ends 438 of platform 414 can function as handles to facilitate simple and convenient use of fluid sampling device 400. Walls 422 are disposed on opposing sides of platform 414. The ends of wall 422 are rounded in toward the center of base portion 404. Walls 422 have first ridges 424 and second ridges 428 extending along their outer surfaces. As seen best in FIG. 10A, first ridges 424 are vertically above second ridges 428 and extend further out than second ridges 428. Extending from bottom surface 420 is blunt cannula 426. Blunt cannula 426 has a lumen 430 extending from a distal end of blunt cannula 426 through an aperture 436 in platform 414. The distal end of blunt cannula 426 is adapted to be inserted into sample port 126 to obtain a fluid sample, such as a blood sample.

FIG. 11 is a cross-sectional end view of fluid sampling device 400 illustrating how top portion 402 and base portion 404 couple together. As noted above, the ends of wall 422 and flanges 410 are rounded. The rounded ends of walls 422 and flanges 410 facilitate alignment of top portion 402 and base portion 404 and prevent horizontal movement of top portion 402 relative to base portion 404. The interior surfaces of flanges 410 each has an inwardly projecting ridge 432 that is adapted to engage ridges 424 and 428. Specifically, top portion 402 is aligned with base portion 404 and flanges 410 extend over walls 422 and ridges 432 engage ridges 424 when test strip 226 is disposed between top portion 402 and base portion 404. Top portion 402 is sized such that when test strip 226 is in place and ridges 432 are engaged with ridges 424, flanges 410 are deflected slightly away from base portion 404. When test strip 226 is removed, the deflection in flanges 410 causes top portion 402 to be biased toward base portion 404. Therefore, when test strip 226 is removed, top portion 402 moves toward base portion 404 until bottom surface 408 of top portion 402 comes into contact with top surface 416 of platform 414. At this point, ridges 432 of flanges 410 engage ridges 428 of walls 422. The engagement between ridges 432 and either ridges 424 or ridges 428 prevents top portion 402 from becoming undesirably separated from base portion 404. In embodiments in which top portion 402 comprises test strip 226, test strip 226 can be coupled to base portion 404 with a flange similar to flanges 410, or test strip 226 can be bonded to base portion 404 with a glue or plastic.

In use, fluid sampling device 400 will have test strip 226 inserted between top portion 402 and base portion 404. After fluid drawing device 100 has been activated and a fluid has been drawn into IV tube 102 past sample port 126, a user can insert the distal end of blunt cannula 426 into sample port 126. Pressure, such as hydrostatic, hemodynamic, or mechanically induced pressure, causes fluid from sample port 126 to enter lumen 430 and move up through base portion 404 and onto test strip 226. When a sufficient fluid sample has been obtained, fluid sampling device 400 can be removed from sample port 126. Test strip 226 can then be withdrawn from between top portion 402 and base portion 404 and analyzed in a glucometer as described above. In embodiments in which test strip 226 comprises top portion 402, fluid sampling device 400 can be removed from sample port 126 after a fluid sample has been obtained and a glucometer modified to receive fluid sampling device 400 can be used to analyze the fluid sample. In some embodiments in which test strip 226 comprises top portion 402, test strip 226 can be removed from base portion 404 and the fluid sample can be analyzed with a standard glucometer.

When fluid, such as blood, is drawn from sample port 126 into fluid sampling device 400, excess fluid may be received within fluid sampling device 400 and on test strip 226. To prevent excess fluid from leaking out of fluid sampling device 400 or remaining on test strip 226 when it is removed from fluid sampling device 400, top portion 402 has recess 412 and base portion 404 has grooves 418 in top surface 416 that cooperate to eliminate these problems. Specifically, grooves 418 act like a squeegee to remove excess fluid from test strip 226 as test strip 226 is withdrawn from fluid sampling device 400. When test strip 226 is removed from fluid sampling device 400, top portion 402 and base portion 404 come together as described above, and grooves 418 and recess 412 cooperate to retain the excess fluid within fluid sampling device 400.

Figure 12:
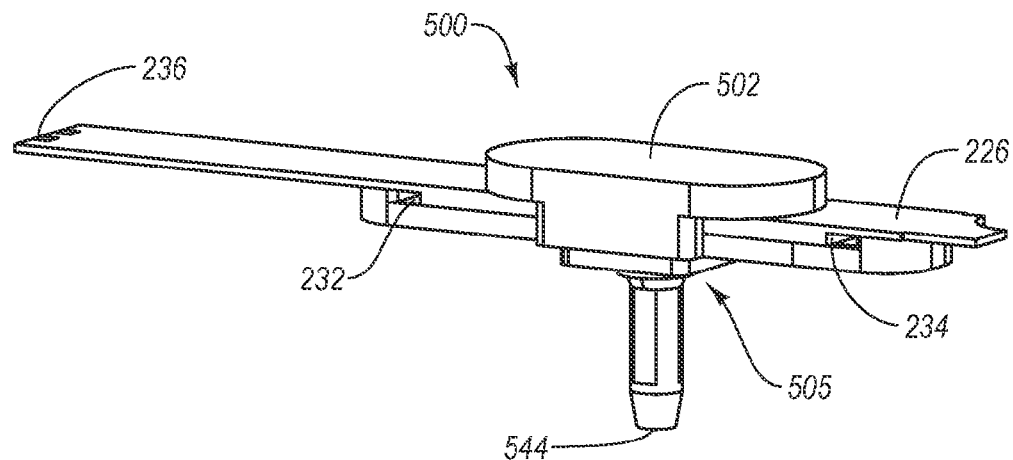
FIG. 12 illustrates a perspective view of a fluid sampling device according to another embodiment of the present invention.

FIG. 12 illustrates a perspective view of yet another embodiment of a fluid sampling device, generally denoted at 500. Fluid sampling device 500 of the present embodiment comprises a top portion 502 and a base portion 504 that are adapted to be coupled together in the same manner as top portion 402 and base portion 404, as illustrated in FIG. 11. Top portion 502 is identical to top portion 402 illustrated in FIGS. 9A-9C. Likewise, base portion 504 is similar to base portion 404 illustrated in FIGS. 10A-10C. Also like fluid sampling device 400, top portion 502 and base portion 504 are adapted to receive test strip 226 therebetween. It is contemplated that standard test strips having electrical connections 236, such as the One Touch Ultra test strip made by LifeScan® (a Johnson & Johnson subsidiary) or the Comfort Curve test strip made by Accu-Chek (a Roche subsidiary) can be used in combination with fluid sampling device 500. Fluid sampling device 500 can also be configured for insertion within sample port 126 to obtain a fluid sample in the same manner as fluid sampling device 400 as illustrated in FIG. 1.

Figure 13A:
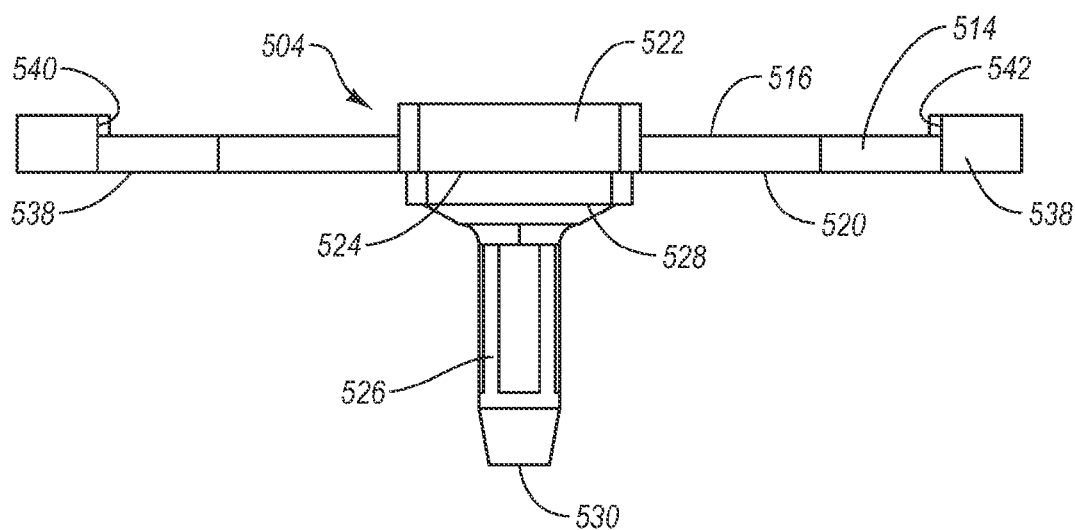
FIG. 13A illustrates a side view of the base portion of the fluid sampling device of FIG. 12.
Figure 13B:
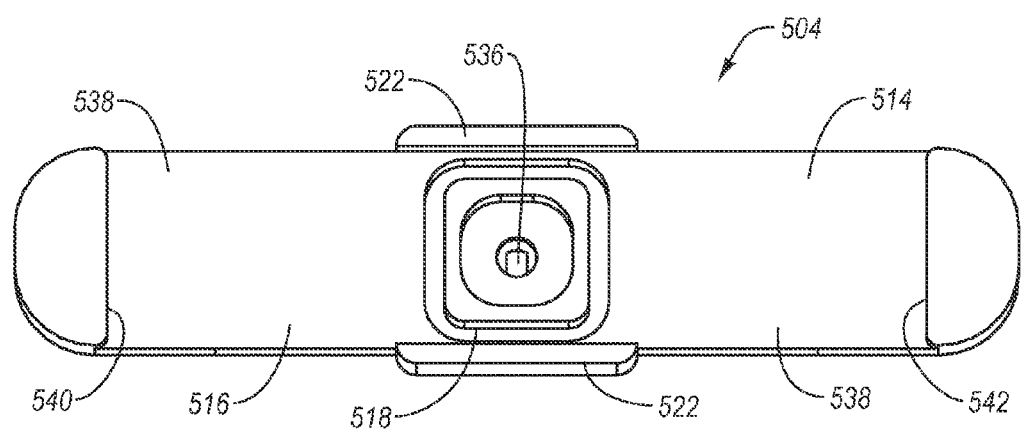
FIG. 13B illustrates a top view of the base portion of the fluid sampling device of FIG. 12.

FIGS. 13A and 13B illustrate side and top views of base portion 504. Base portion 504 comprises a platform 514, walls 522, and a blunt cannula 526. Platform 514 has a bottom surface 520 and a top surface 516 with groove 518 therein as seen in FIG. 13B. The opposing ends 538 of platform 514 can function as handles to facilitate simple and convenient use of fluid sampling device 500. Opposing ends 538 of platform 514 also have retention walls 540 and 542 extending upwardly from top surface 516. Retention walls 540 and 542 are adapted to abut edges 232 and 234 of test strip 226 (FIG. 12) to prevent test strip 226 from being removed from between top portion 502 and base portion 504. In addition to retention walls 540 and 542, test strip 226 can be coupled to top portion 502 and/or base portion 504 with an adhesive such as glue, or a mechanical fastener.

Walls 522 of base portion 504 are disposed on opposing sides of platform 514. The ends of wall 522 are rounded in toward the center of base portion 504. Walls 522 have first ridges 524 and second ridges 528 extending along their outer surfaces. First ridges 524 are vertically above second ridges 528 and extend further out than second ridges 528 in the same manner as first ridges 424 and second ridges 428 as illustrated in FIG. 10A. Walls 522 and first and second ridges 524 and 528 facilitate coupling of base portion 504 to top portion 502 in a manner similar to that of top portion 402 and base portion 404 as illustrated in FIG. 11.

Extending from bottom surface 520 of base portion 504 is blunt cannula 526. Blunt cannula 526 has a lumen 530 extending from a distal end of blunt cannula 526 through an aperture 536 in platform 514. The distal end of blunt cannula 526 is adapted to be inserted into sample port 126 (FIG. 1) to obtain a fluid sample, such as a blood sample. Blunt cannula 526 can also include a one-way valve 544 (not shown) to prevent or limit the reflux of air into the IV tube 102. In one embodiment, valve 544 is coupled to the distal end of lumen 530. Valve 544 can also be disposed in other positions within lumen 530. Valve 544 can be made of a medical grade plastic and/or rubber.

In use, fluid sampling device 500 will have test strip 226 inserted between top portion 502 and base portion 504. After fluid drawing device 100 has been activated and a fluid has been drawn into IV tube 102 past sample port 126, a user can insert the distal end of blunt cannula 526 into sample port 126. Pressure, such as hydrostatic, hemodynamic, or mechanically induced pressure, causes fluid from sample port 126 to enter lumen 530 and move up through base portion 504 and onto test strip 226. Groove 518 is disposed adjacent aperture 536 and test strip 226 to facilitate the escape of air from test strip 226, thus enabling the fluid sample to readily flow into test strip 226. When a sufficient fluid sample has been obtained, fluid sampling device 500 can be removed from sample port 126. Electrical connections 236 can then be inserted into a glucometer, such as glucometer 900 illustrated in FIG. 21, for analysis. Glucometers, such as glucometer 900, are adapted to analyze various properties of the fluid sample absorbed by test strip 226 by determining the electrical properties, such as the resistance, of the fluid sample.

When fluid, such as blood, is drawn from sample port 126 into fluid sampling device 500, excess fluid may be received within fluid sampling device 500 and on test strip 226. In some embodiments it may be desirable to remove excess fluid from test strip 226. Groove 518 of base portion 504 can also be adapted to receive excess fluid received within fluid sampling device 500. In the illustrated embodiment, groove 518 extends around aperture 536 to receive excess fluid that flows into fluid sampling device 500 through lumen 530. It will be appreciated that groove 518 can comprise multiple concentric grooves, or any other configuration of one or more grooves that are adapted to receive excess fluid in fluid sampling device 500.

Figure 14:
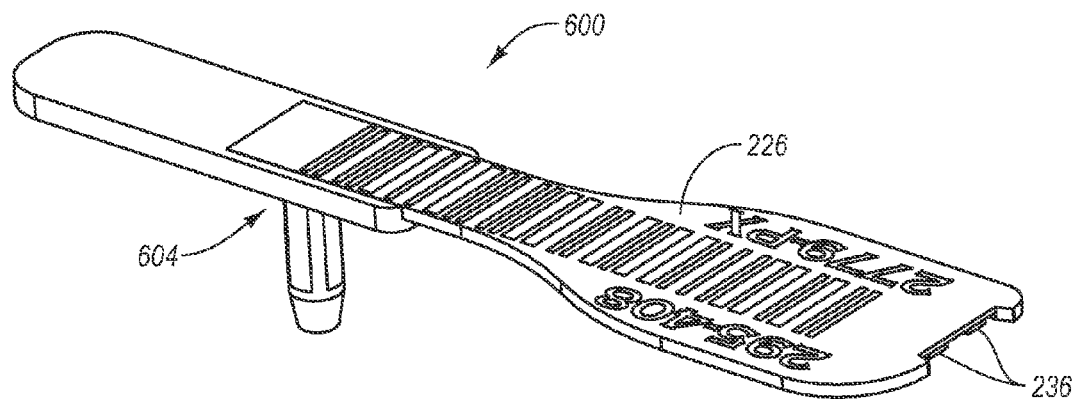
FIG. 14 illustrates a perspective view of a fluid sampling device according to another embodiment of the present invention.

FIG. 14 illustrates a perspective view of still yet another embodiment of a fluid sampling device, generally denoted at 600. Fluid sampling device 600 of the present embodiment comprises a test strip 226 and a base portion 604 that are adapted to be coupled together. Test strip 226 can be any one of a variety of test strips having electrical connections 236 or other means for analyzing properties of the fluid sample received by fluid sampling device 600. For example, test strip 226 could be a One Touch Ultra test strip made by LifeScan® (a Johnson & Johnson subsidiary) or a Comfort Curve test strip made by Accu-Chek (a Roche subsidiary). Base portion 604 has a configuration similar to base portions 404 and 504 of the previous embodiments. Fluid sampling device 600 can also be configured for insertion within sample port 126 to obtain a fluid sample in the same manner as the previously discussed fluid sampling devices.

Figure 15:
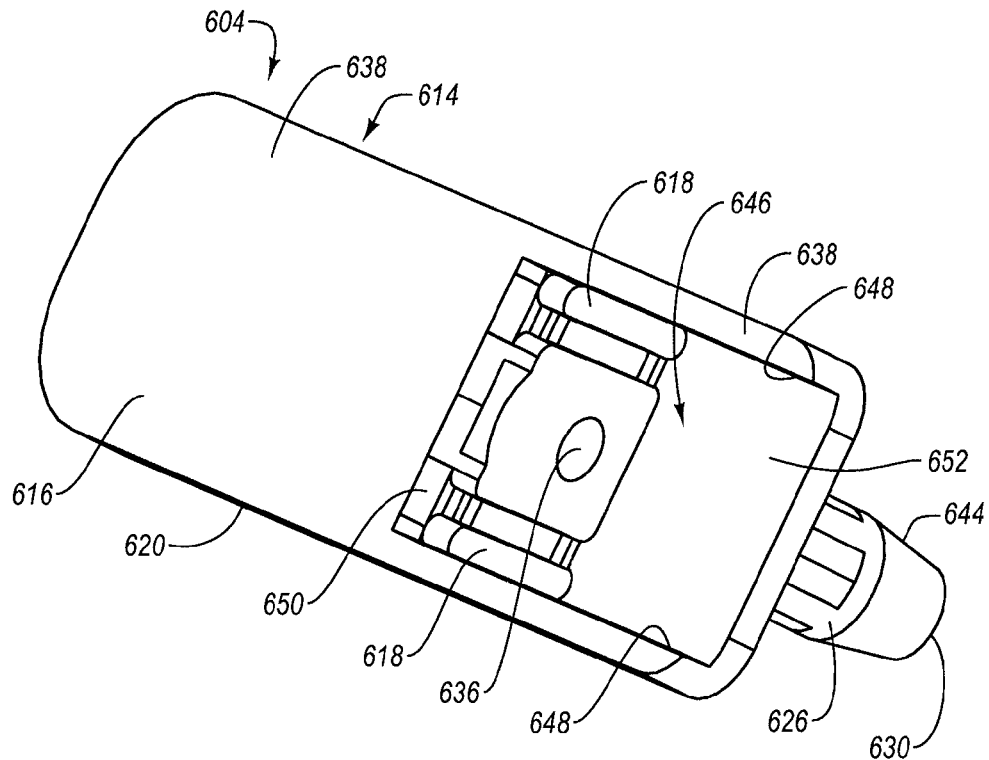
FIG. 15 illustrates a perspective view of the base portion of the fluid sampling device of FIG. 14.

FIG. 15 illustrates a top perspective view of base portion 604. Base portion 604 comprises a platform 614, mounting portion 646, and a blunt cannula 626. Platform 614 has a bottom surface 620 and a top surface 616. Mounting portion 646 extends from a first end of base portion 604 to about the middle of base portion 604, and is generally defined by opposing side walls 648, end wall 650, and support surface 652. Support surface 652 has grooves 618 therein for receiving excess fluid in that same manner as groove 518 of fluid sampling device 500. Opposing side walls 648, end wall 650, and support surface 652 are adapted to abut edges of test strip 226 such that the shape of mounting portion 646 corresponds to the shape of test strip 226 so as to assist in maintaining test strip 226 in a desired position. In addition, test strip 226 can be coupled to base portion 604 with an adhesive such as glue, or a mechanical fastener. The opposing ends 638 of platform 614 can function as handles to facilitate simple and convenient use of fluid sampling device 600.

Extending from bottom surface 620 of base portion 604 is blunt cannula 626. Blunt cannula 626 has a lumen 630 extending from a distal end of blunt cannula 626 through aperture 636 in support surface 652. In the illustrated embodiment, blunt cannula 626 is offset toward one end of platform 614, however, it will be appreciated that base portion 604 can be configured with blunt cannula 626 extending from platform 614 in other locations to accommodate various test strips 226. The distal end of blunt cannula 626 is adapted to be inserted into sample port 126 (FIG. 1) to obtain a fluid sample, such as a blood sample. Blunt cannula 626 can also include a one-way valve 644 (not shown) to prevent or limit the reflux of air into IV tube 102. In one embodiment, valve 644 is coupled to the distal end of lumen 630. Valve 644 can also be disposed in other positions within lumen 630. Valve 644 can be made of a medical grade plastic and/or rubber.

In use, fluid sampling device 600 will have test strip 226 coupled to base portion 604 within mounting portion 646. After fluid drawing device 100 has been activated and a fluid has been drawn into IV tube 102 past sample port 126, a user can insert the distal end of blunt cannula 626 into sample port 126. Pressure, such as hydrostatic, hemodynamic, or mechanically induced pressure, causes fluid from sample port 126 to enter lumen 630 and move up through base portion 604 and onto test strip 226. Grooves 618 are disposed adjacent aperture 636 and test strip 226 to facilitate the escape of air from test strip 226, thus enabling the fluid sample to readily flow into test strip 226. When a sufficient fluid sample has been obtained, fluid sampling device 600 can be removed from sample port 126. Electrical connections 236 can then be inserted into a glucometer, such as glucometer 900 illustrated in FIG. 21, for analysis. Glucometers, such as glucometer 900, are adapted to analyze various properties of the fluid sample absorbed by test strip 226 by determining the electrical properties, such as the resistance, of the fluid sample.

When fluid, such as blood, is drawn from sample port 126 into fluid sampling device 600, excess fluid may be received within fluid sampling device 600. In some embodiments it may be desirable to remove excess fluid received within fluid sampling device 600 from test strip 226. Grooves 618 of base portion 604 can also be adapted to receive excess fluid received within fluid sampling device 600. In the illustrated embodiment, grooves 618 extend parallel to each other on two opposing sides of aperture 636 to receive excess fluid that flows into fluid sampling device 600 through lumen 630. It will be appreciated that grooves 618 can comprise one or more grooves that extend around at least a part of aperture 636.

Figure 16:
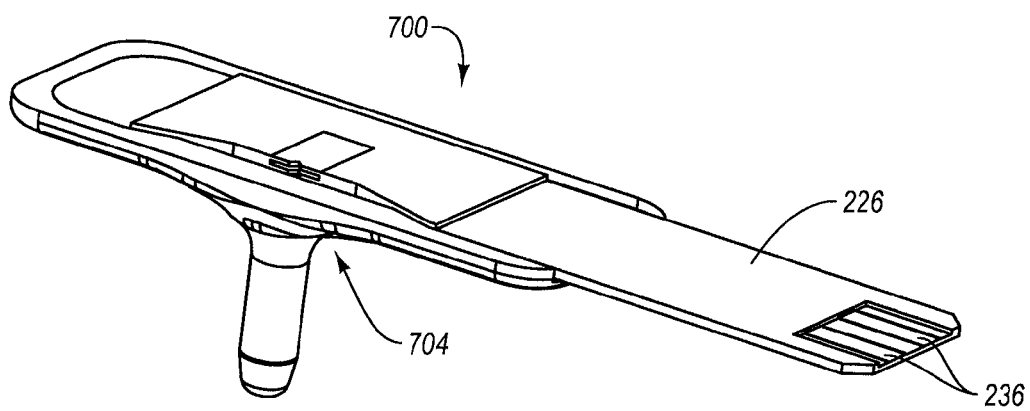
FIG. 16 illustrates a perspective view of a fluid sampling device according to another embodiment of the present invention.

FIG. 16 illustrates a perspective view of still yet another embodiment of a fluid sampling device, generally denoted at 700. Fluid sampling device 700 of the present embodiment comprises a test strip 226 and a base portion 704 that are adapted to be coupled together. Base portion 704 has a configuration similar to base portion 604. Fluid sampling device 700 can also be configured for insertion within sample port 126 to obtain a fluid sample in the same manner as the previously discussed fluid sampling devices.

Figure 17A:
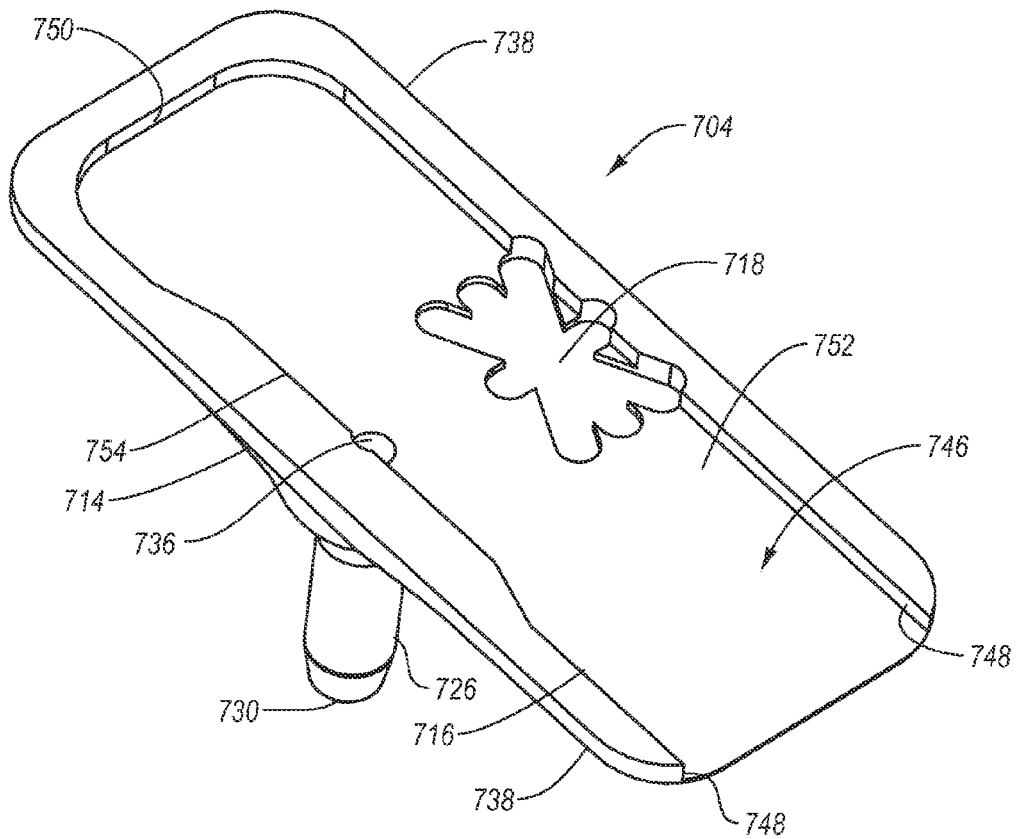
FIG. 17A illustrates a top perspective view of the base portion of the fluid sampling device of FIG. 16.
Figure 17B:
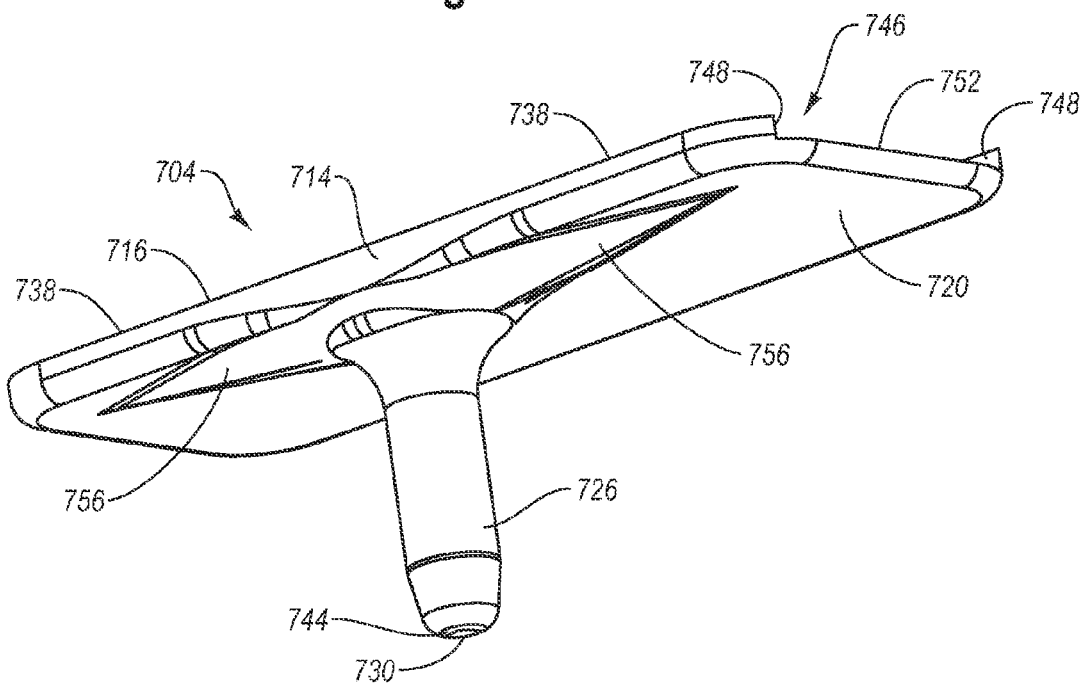
FIG. 17B illustrates a bottom perspective view of the base portion of the fluid sampling device of FIG. 16.

FIGS. 17A and 17B illustrate top and bottom perspective views of base portion 704. Base portion 704 comprises a platform 714, mounting portion 746, and a blunt cannula 726. Platform 714 has a bottom surface 720 and a top surface 716. Mounting portion 746 is generally defined by opposing side walls 748, end wall 750, and support surface 752. Support surface 752 has grooves 718 therein for venting air from test strip 226 as described below. Opposing side walls 748, end wall 750, and support surface 752 are adapted to abut edges of test strip 226 to assist in maintaining test strip 226 in a desired position. One or both of side walls 748 can include a projecting portion 754 that extends toward the middle of mounting portion 746. In this manner, mounting portion 746 can be configured to fit around specific shaped test strips 226, as illustrated in FIG. 16. In addition, test strip 226 can be coupled to base portion 704 with an adhesive such as glue, or a mechanical fastener. The opposing ends 738 of platform 714 can function as handles to facilitate simple and convenient use of fluid sampling device 700.

Extending from bottom surface 720 of base portion 704 is blunt cannula 726. Blunt cannula 726 has a lumen 730 extending from a distal end of blunt cannula 726 through aperture 736 in support surface 752. In the illustrated embodiment, blunt cannula 726 is offset toward one side of platform 714 to accommodate test strip 226 as described below. However, it will be appreciated that base portion 704 can be configured with blunt cannula 726 extending from platform 714 in other locations. The distal end of blunt cannula 726 is adapted to be inserted into sample port 126 (FIG. 1) to obtain a fluid sample, such as a blood sample. Blunt cannula 726 can also include a one-way valve 744 to prevent or limit the reflux of air into IV tube 102. In the illustrated embodiment, valve 744 is coupled to the distal end of lumen 730. It will be appreciated that valve 744 can also be disposed in other positions within lumen 730. Valve 744 can be made of a medical grade plastic and/or rubber. Also disposed on bottom surface 720 are alignment members 756 which extend from blunt cannula 726 toward opposing ends of platform 714. Alignment members 756 provide a reference point to enable a user to center the blunt cannula 726 in their fingers and to determine the center position of the offset blunt cannula 726. Alignment members 756 also add additional mass, and thus strength, to fluid sampling device 700.

Figure 18A:
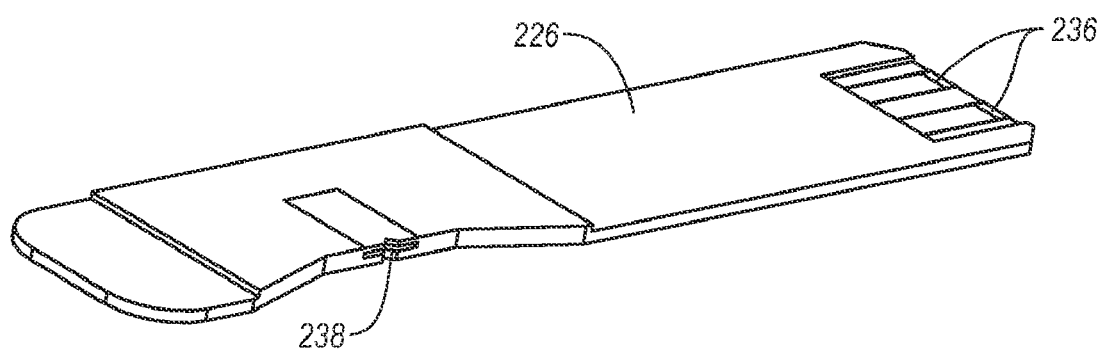
FIG. 18A illustrates a top perspective view of the test strip of the fluid sampling device of FIG. 16.
Figure 18B:
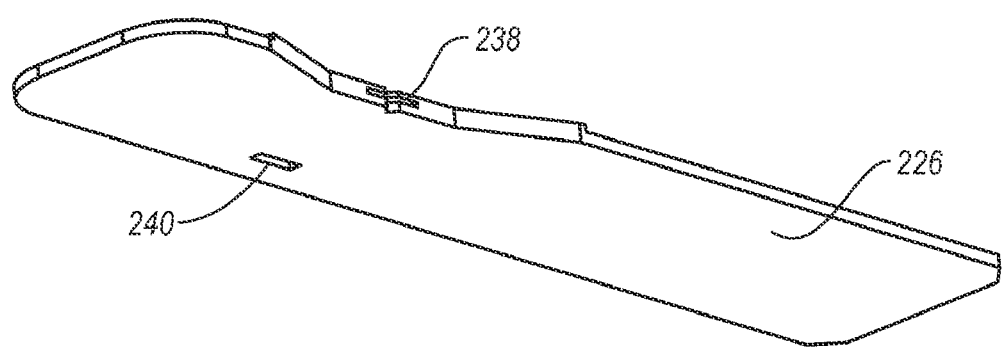
FIG. 18B illustrates a bottom perspective view of the test strip of the fluid sampling device of FIG. 16.

FIGS. 18A and 18B illustrate one example embodiment of test strip 226 that can be used with fluid sampling device 700. The illustrated embodiment of test strip 226 is a Comfort Curve test strip made by Accu-Chek (a Roche subsidiary). However, test strip 226 can be any one of a variety of test strips having electrical connections 236 or other means for analyzing properties of the fluid sample received by fluid sampling device 700, such as the One Touch Ultra test strip made by LifeScan® (a Johnson & Johnson subsidiary).

Test strip 226 includes electrical connections 236, fluid intake 238, and vent 240. As discussed herein, electrical connections 236 can be used in conjunction with a glucometer to analyze the fluid sample retrieved with fluid sampling device 700. Fluid intake 238 can be an opening in the side, or other surface, of test strip 226. Fluid intake 238 is adapted to receive a fluid sample, such as blood, therein. To enable a fluid to readily flow into fluid intake 238, the air disposed within fluid intake 238 must be removed. Vent 240 is in fluid communication with fluid intake 238 and allows the air in fluid intake 238 to escape therefrom as a fluid sample enters fluid into 238.

In use, fluid sampling device 700 will have test strip 226 coupled to base portion 704 within mounting portion 746. After fluid drawing device 100 has been activated and a fluid has been drawn into IV tube 102 past sample port 126, a user can insert the distal end of blunt cannula 726 into sample port 126. Pressure, such as hydrostatic, hemodynamic, or mechanically induced pressure, causes fluid from sample port 126 to enter lumen 730 and move up through aperture 736 of base portion 704. The fluid sample then enters fluid intake 238 of test strip 226. Air within fluid intake 238 can escape test strip 226 through vent 240. Grooves 718 are disposed adjacent vent 240 to facilitate the escape of air from test strip 226 through vent 240, thus enabling the fluid sample to readily flow into test strip 226. When a sufficient fluid sample has been obtained, fluid sampling device 700 can be removed from sample port 126. Electrical connections 236 can then be inserted into a glucometer, such as glucometer 900 illustrated in FIG. 21, for analysis. Glucometers, such as glucometer 900 are adapted to analyze various properties of the fluid sample absorbed by test strip 226 by determining the electrical properties, such as the resistance, of the fluid sample.

When fluid, such as blood, is drawn from sample port 126 into fluid sampling device 700, excess fluid may be received within fluid sampling device 600. In some embodiments it may be desirable to remove excess fluid received within fluid sampling device 700 from test strip 226. Grooves 718 can also be adapted to receive excess fluid received within fluid sampling device 700. In the illustrated embodiment, grooves 618 extend parallel to each other on two opposing sides of aperture 636 to receive excess fluid that flows into fluid sampling device 600 through lumen 630. It will be appreciated that grooves 618 can comprise one or more grooves that extend around at least a part of aperture 636.

As with fluid drawing device 100, fluid sampling devices 200, 400, 500, 600, and 700 can be made from medical device industry standard plastics including, but not limited to thermoplastics, such as Polyethylene (PE), High Density Polyethylene (HDPE), Polypropylene (PP), Polystyrene (PF), Polyethylene Terephthalate (PET), and acrylic (for transparent properties), because of their low cost production, ability to be easily molded, sterility, and strength.

Figure 19:
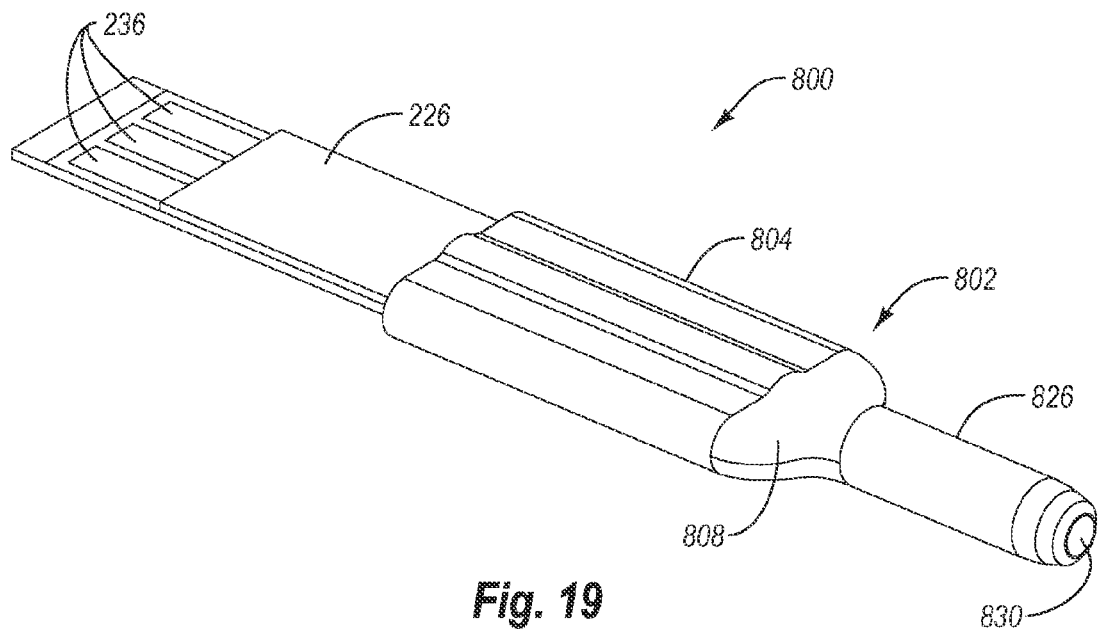
FIG. 19 illustrates a perspective view of a fluid sampling device according to yet another embodiment of the present invention.

FIG. 19 illustrates a perspective view of still yet another embodiment of a fluid sampling device, generally denoted at 800. Fluid sampling device 800 of the present embodiment comprises a test strip 226 and a test strip housing 802. Test strip housing 802 includes a blunt cannula 826 and a test strip receptacle 804 for receiving at least a portion of test strip 226 therein. Test strip 226 can be any one of a variety of test strips having electrical connections 236 or other means for analyzing properties of a fluid sample received by fluid sampling device 800. For example, test strip 226 could be a One Touch Ultra test strip made by LifeScan® (a Johnson & Johnson subsidiary) or a Comfort Curve test strip made by Accu-Chek (a Roche subsidiary). Fluid sampling device 800 can also be configured for insertion within sample port 126 to obtain a fluid sample in a manner similar to that of the previously discussed fluid sampling devices.

Figure 20:
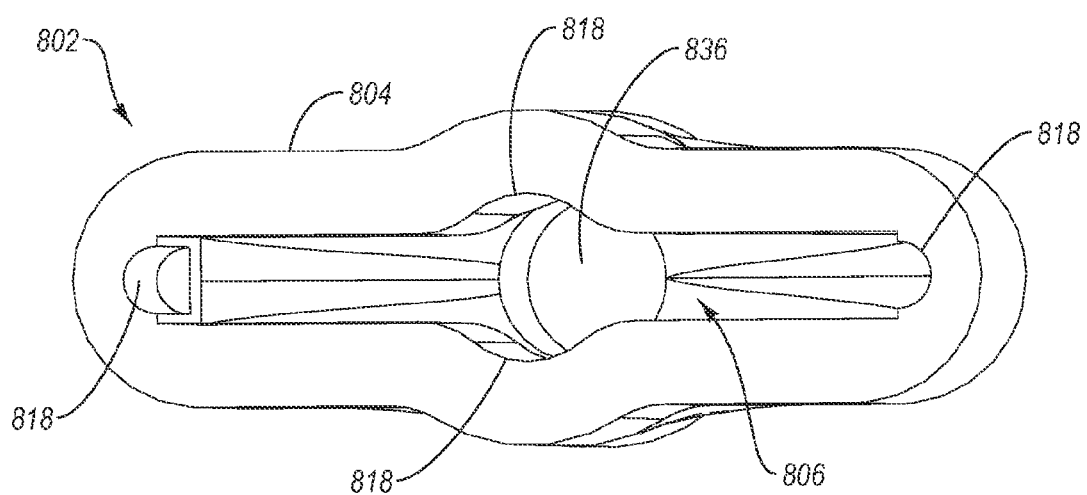
FIG. 20 illustrates an end view of the housing portion of the fluid sampling device of FIG. 19.

As illustrated in FIGS. 19 and 20, test strip receptacle 804 has a generally flat, rectangular shape with an interior portion 806. Interior portion 806 is adapted to receive at least a portion of test strip 226 therein. In the illustrated embodiment, interior portion 806 is sized and configured to generally correspond to the size and shape of test strip 226 such that an end of test strip 226 can be inserted and maintained within test strip receptacle 804. Test strip 226 can be held within interior portion 806 of test strip receptacle 804 by a variety of means, including frictional coupling, mechanical fasteners such as clamps or pins, and adhesives such as glue. In addition, test strip receptacle 804 can function as a handle to facilitate simple and convenient use of fluid sampling device 800.

As can be seen in FIG. 20, the walls of interior portion 806 include grooves 818 which provide similar functionality as the grooves described elsewhere herein. In particular, grooves 818 are adapted to assist in venting air from test strip 226 to enable test strip 226 to readily absorb a fluid sample. In the exemplary embodiment, grooves 818 extend from the opening of interior portion 806 to about the opposing end of test strip receptacle 804. However, it will be appreciated that grooves 818 can be otherwise configured. For example, grooves 818 can comprise a single groove or grooves 818 can be completely disposed within test strip housing 802.

Extending from an end of test strip receptacle 804 is a connecting portion 808. Connecting portion 808 is generally funnel shaped and connects test strip receptacle 804 to blunt cannula 826. Blunt cannula 826 has a lumen 830 extending from a distal end of blunt cannula 826 through aperture 836 in connecting portion 808. Test strip receptacle 804, connecting portion 808, and blunt cannula 826 can be made from discrete parts and coupled together, such as with an adhesive, or they can be formed as a single integral piece. The distal end of blunt cannula 826 is adapted to be inserted into sample port 126 (FIG. 1) to obtain a fluid sample, such as a blood sample. Blunt cannula 826 can also include a one-way valve 844 (not shown) to prevent or limit the reflux of air into IV tube 102. In one embodiment, valve 844 is coupled to the distal end of lumen 830. Valve 844 can also be disposed in other positions within lumen 830. Valve 844 can be made of a medical grade plastic and/or rubber.

In use, fluid sampling device 800 will have test strip 226 coupled within interior portion 806 of test strip receptacle 804. After fluid drawing device 100 has been activated and a fluid has been drawn into IV tube 102 past sample port 126, a user can insert the distal end of blunt cannula 826 into sample port 126. Pressure, such as hydrostatic, hemodynamic, or mechanically induced pressure, causes fluid from sample port 126 to enter lumen 830 and move up through blunt cannula 826 and connecting portion 808 and onto test strip 226. Grooves 818 are disposed adjacent test strip 226 to facilitate the escape of air from test strip 226, thus enabling the fluid sample to readily flow into test strip 226. When a sufficient fluid sample has been obtained, fluid sampling device 800 can be removed from sample port 126. Electrical connections 236 of test strip 226 can then be inserted into a glucometer, such as glucometer 900 illustrated in FIG. 21, for analysis. Glucometers, such as glucometer 900, are adapted to analyze various properties of the fluid sample absorbed by test strip 226 by determining the electrical properties, such as the resistance, of the fluid sample.

While the foregoing exemplary fluid sampling devices have been illustrated and described as comprising multiple discrete parts that are coupled together, it will be appreciated that each of the various fluid sampling devices disclosed herein can also be formed as a single integral piece. For example, base portions 504, 604, and 704 and test strip housing 802 can each be formed with an integrated test strip or other fluid monitoring technology. For example, the fluid sampling devices disclosed herein can be formed with an interior cavity or chamber which is in fluid communication with a blunt cannula. A fluid monitoring device, such as absorbent material 220 or electrical connections 236, can be at least partially disposed within or in fluid communication with the cavity such that various attributes of the fluid sample can be detected without the use of a conventional test strip.

Figure 21:
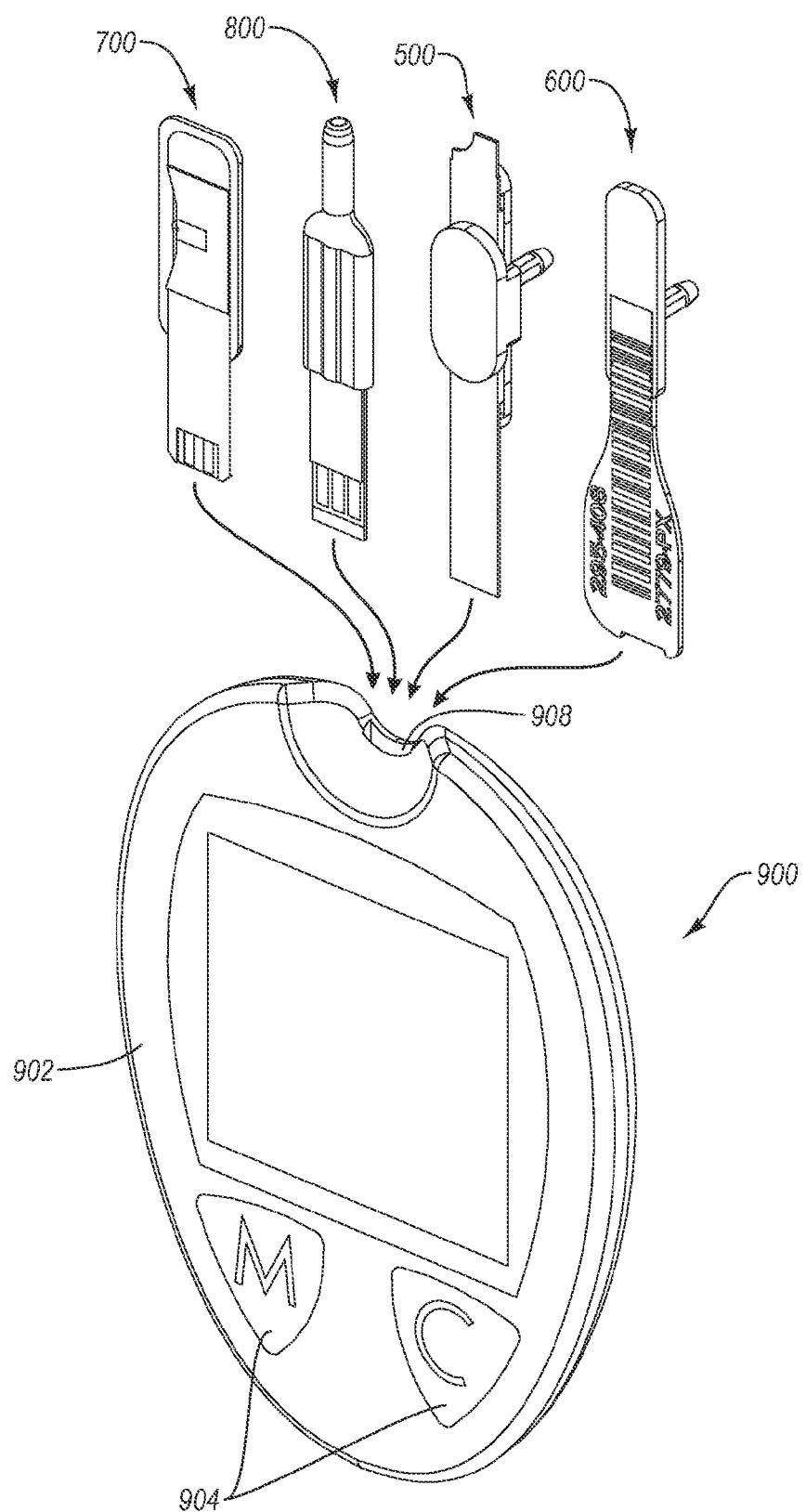
FIG. 21 illustrates a exemplary fluid sampling devices according to the present invention associated with a glucometer.

Having obtained a fluid sample within one of fluid sampling devices 500, 600, 700, and 800, the fluid sample can then be analyzed using a glucometer 900 as seen in FIG. 21. Glucometers are well known in the art. A typical glucometer 900 comprises a housing 902, keys 904, internal analysis apparatus 906 (not shown), and a receptacle 908 for receiving a test strip having a fluid sample, such as a blood sample, disposed thereon. The glucometer shown in FIG. 21 has a receptacle 908 that is designed to receive an end of test strip 226 therein. Disposed within receptacle 908 are electrical connections (not shown) which are adapted for electrical communication with electrical connections 236 of test strip 226 when the end of test strip 226 is inserted within receptacle 908. The internal analysis apparatus 906 of glucometer 900 is adapted to analyze various electrical properties of the fluid sample received on test strip 226. Such electrical properties can include the resistance, impedance, capacitance and the like of the fluid sample. Glucometer 900 is adapted to determine various attributes of the fluid sample, such as the glucose level of a blood sample, based on the electrical properties of the fluid sample.

Figure 22A:
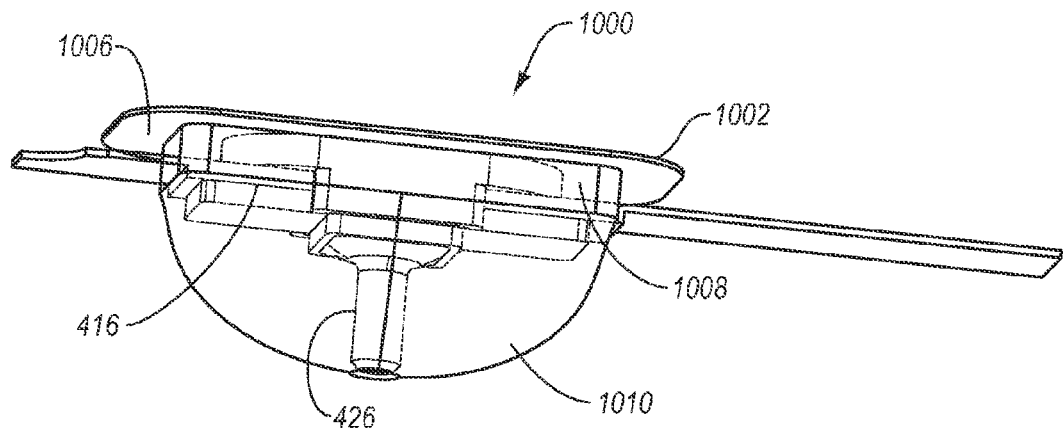
FIG. 22A illustrates a perspective view of a fluid sampling device according to one embodiment of the present invention disposed within a protective packaging.
Figure 22B:
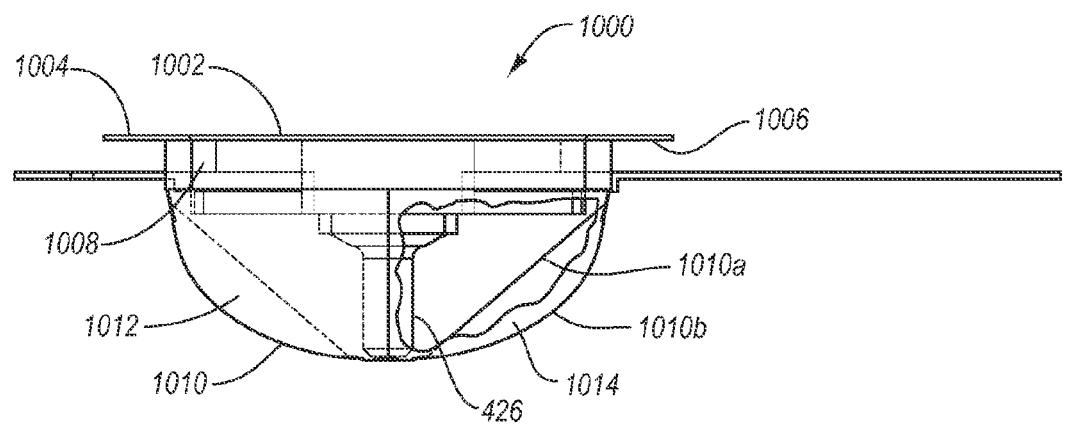
FIG. 22B illustrates a partial cross-sectional view of the protective packaging of FIG. 22A.

FIGS. 22A-22B illustrate an example embodiment of a protective housing 1000 that is adapted to receive one of fluid sampling devices 400, 500, 600, 700, and 800 therein. The example embodiment of protective housing 1000 is shown and described with specific reference to fluid sampling device 400. However, it will be appreciated that protective housing 1000 can be employed with any one of fluid sampling devices 400, 500, 600, 700, and 800, either as described herein or with minor modifications that will be readily apparent to one of ordinary skill in the art.

In the illustrated embodiment, protective housing 1000 comprises substrate 1002, a railing 1008, and a cover portion 1010. Substrate 1002 has a top surface 1004 and a bottom surface 1006 that lays adjacent top surface 406 of top portion 402. Extending from bottom surface 1006 is railing 1008. Railing 1008 extends around fluid sampling device 400 and down to about top surface 416 of platform 414. Substrate 1002 and railing 1008 can be formed as a unitary piece, or can be individually formed and coupled together.

Attached to the lower edge of railing 1008 is cover portion 1010. Cover portion 1010 extends over blunt cannula 426. Cover portion 1010 can comprise two layers of plastic 1010a and 1010b with air disposed therebetween. Layers of plastic 1010a and 1010b can be bonded together at various points to create pockets of air therein. As shown in FIG. 22B, layers of plastic 1010a and 1010b are bonded together near railing 1008 and the distal end of blunt cannula 426, thus creating air pockets 1012 and 1014. In some embodiments, cover portion 1010 comprises a single layer of plastic 1010a that extends from railing 1008 around base portion 404.

Protective housing 1000 is adapted to protect fluid sampling device 400 from physical damages prior to use, such as during shipment. Protective housing 1000 also maintains the sterility of fluid sampling device 400 by preventing undesirable contamination through exposure to a non-sterile surface, such as a user's hands.

Fluid sampling device 400 packaged in protective housing 1000 is used in a manner similar to that described above with respect to fluid sampling device 400. However, when fluid sampling device 400 is packaged in protective housing 1000, cover portion 1010 must be ruptured prior to inserting blunt cannula 426 into sample port 126. Typically, a user will hold fluid sampling device 400, disposed within protective packaging 1000, with their thumb or palm on top surface 1004 of substrate 1002, and their index and middle fingers extending around opposing sides of cover portion 1010. Holding fluid sampling device 400 and protective housing 1000 in this manner, a user can squeeze protective housing 1000 with enough force to rupture air pockets 1012 and 1014. Once air pockets 1012 and 1014 have been ruptured, the distal end of blunt cannula 426 can be forced through layers of plastic 1010a and 1010b to expose blunt cannula 426. With blunt cannula 426 exposed, a user can then insert blunt cannula into sample port 126 to obtain a fluid sample in the same manner as previously described.

In some embodiments, one or both of layers of plastic 1010a and 1010b of cover portion 1010 can be formed of a resilient material, such as a semi-rigid plastic, a shape memory material, a foam, or a rubber material. When employing a resilient cover portion 1010, a user can obtain a fluid sample in a manner similar to that described above (i.e., compress cover portion 1010 until blunt cannula 426 extends through cover portion 1010 and insert blunt cannula 426 into sample port 126). However, unlike the previously described embodiments, a resilient cover portion 1010 can regain its shape after the user removes pressure from cover portion 1010. As cover portion 1010 regains its original shape, blunt cannula 426 is once again enclosed within cover portion 1010. Thus, protective housing 1000 can be configured so as to expose blunt cannula 426 when being inserted into sample port 126. Reducing the time that blunt cannula 426 is exposed, both before and after use, provides numerous benefits. As discussed above, protective housing 1000 can prevent contamination of blunt cannula 426 prior to use. Additionally, use of a resilient cover portion 1010 can also reduce the risk of exposure to a user, such as a nurse, by enclosing blunt cannula 426, and any excess fluid thereon, within protective housing 1000.

As noted above, each of fluid sampling devices 400, 500, 600, 700, and 800 can be disposed within protective housing 1000. As is readily apparent to one of ordinary skill in the art, various modifications can be made to protective housing 1000 to accommodate various embodiments of fluid sampling devices. For example, when protective housing 1000 is utilized with fluid sampling devices 600 or 700, bottom surface 1006 of substrate 1002 lays adjacent test strip 226 and top surface 616 or 716 rather than top portion 402 or 502. Similarly, substrate 1002 can also function to enclose the opening between aperture 736 and fluid intake 238 to assist in directing fluid received through blunt cannula 726 into fluid intake 238 of test strip 226. Substrate 1002 can also assist in preventing fluid received within fluid sampling device 700 from leaking out of fluid sampling device 1000.

In one embodiment, the fluid drawing device can comprise a housing having a fill chamber in fluid communication with a patient injection site. A piston can be positionable within the fill chamber to sealingly engage the fill chamber, wherein the piston has a first position and a second position, wherein movement of the piston from the first position to the second position generates a negative pressure in the fill chamber effective to draw fluid from the patient injection site into the fill chamber. The fluid drawing device can also include biasing means for biasing the piston to the second position relative to the first position. The biasing means can comprise a spring linked to the piston, such that the spring is more compressed when the piston is in the first position than when the piston is in the second position. In some embodiments, the biasing means is generated by fluid pressure from the patient injection site. In other embodiments, the biasing means is generated by hydraulic actuation. The fluid drawing device can also include securing means for selectively securing the piston in the second position. The securing means can comprise a locking system at least partially coupled to the piston.

In an alternative exemplary embodiment, the fluid drawing device can comprise a housing having a fill chamber in fluid communication with a patient injection site, a piston disposed and positionable within the fill chamber, the piston being sealingly engaged with the fill chamber to generate a negative pressure in the fill chamber effective to draw fluid from the patient injection site into the fill chamber when the piston is moved from a first position to a second position. The fluid drawing device can also include biasing means for biasing the piston to the second position relative to the first position, and securing means for selectively securing the piston in the first position. The biasing means of the fluid drawing device can comprise a spring linked to the piston, such that the spring is more compressed when the piston is in the first position than when the piston is in the second position. The biasing means can also be generated by fluid pressure from the patient injection site. The biasing means can also be generated by hydraulic actuation. The securing means can comprise a locking system at least partially coupled to the piston.

In another alternative example embodiment, the fluid drawing device can comprise a housing having a fill chamber in fluid communication with a patient injection site, a piston positionable within the fill chamber to sealingly engage the fill chamber, wherein the piston has a first position and a second position, wherein movement of the piston from the first position to the second position generates a negative pressure in the fill chamber effective to draw fluid from the patient injection site into the fill chamber, a spring linked to the piston, wherein the spring is more compressed when the piston is in the first position than when the spring is in the second position, such that the spring tends to bias the piston to the second position relative to the first position; and a locking member coupled to the piston to selectively secure the piston in the first position. The locking member can be positionable to engage the housing to secure the piston in the first position. The locking member can be configured for selective disengagement from the housing so as to enable the piston to move between the first and the second positions.

One embodiment, a method of sampling bodily fluid comprises: providing a fluid sampling system, wherein said fluid sampling system comprises an IV tube in fluid communication with a patient injection site, said IV tube having a sample port; a fluid drawing device in fluid communication with said IV tube, said fluid drawing device having a fill chamber and a piston sealingly engaged therein; and a fluid sampling device that is configured to be inserted within said sample port, said fluid sampling device having a blunt cannula; drawing a fluid through said IV tube to sample port by activating fluid drawing device, wherein activation of said fluid drawing device comprises moving said piston relative to said fill chamber such that a negative pressure is generated in fluid drawing device sufficient to draw a fluid through IV tube to said sample port; and obtaining a fluid sample from said sample port by inserting said blunt cannula into said sample port and drawing fluid into said fluid sampling device by hydrostatic or hemodynamic pressure, or negative pressure.

In some embodiments of the method, the fluid drawing device comprises two fill chambers and two pistons. In some embodiments, the fluid drawing device further comprises a handle, a main body having an interior portion, and a window in the main body. In some embodiments the fluid drawing device is adapted to receive a test strip therein. In some embodiments the handle of the fluid drawing device is removable to facilitate removal of the test strip from the fluid drawing device. The fluid sampling device has an absorbent material disposed in the interior portion in some embodiments.

In other embodiments, the fluid sampling device further comprises a base portion having a platform and a ridge extending around at least a portion of an outer surface of the base portion; and a top portion having a flange adapted to engage the ridge to couple the top portion to the base portion. In some embodiments, the fluid sampling device is adapted to receive a test strip between the base portion and the top portion. The fluid sampling device can be configured to allow the test strip to be removed from the fluid sampling device to facilitate analysis of the fluid sample.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a glucose monitoring system adapted for monitoring blood glucose, in which the glucose monitoring system includes a glucometer and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, an improved blood sampling device for coupling to the sample port to permit a blood sample to be deposited onto a test strip for analyzing blood glucose levels, the improved blood sampling device comprising in combination:
- a test strip having one end comprised of an absorbent material and a reagent adapted for detecting blood characteristics indicative of glucose levels, and another end comprised of electrical leads adapted for electronic coupling to the glucometer; and
- a test strip adapter configured for coupling the test strip in fluid communication with the sampling port of the intravenous line, the test strip adapter comprising:
  - a base portion with a platform which has on a top side of the platform an unsealed mounting area, and the bottom side of said platform being joined to a blunt cannula configured for insertion into the sampling port, the blunt cannula providing fluid communication of a blood sample from the sampling port into the mounting area of the platform;
  - the unsealed mounting area being configured to receive said test strip end comprised of the absorbent material and reagent; and
  - said unsealed mounting area of the platform terminating at a point that is adapted to permit coupling of the test strip end comprised of electrical leads to the glucometer when the test strip is inserted in said mounting area without having to remove the test strip from the adapter.

2. The blood sampling device of claim 1 wherein said test strip adapter further comprises grooves formed within said mounting area which are configured to assist in venting air from the test strip to enable blood to readily flow to the mounting area in order to contact said test strip.

3. The blood sampling device of claim 1 further comprising a one-way valve positioned at the blunt cannula and adapted to limit reflux of air into the intravenous line.

4. The blood sampling device of claim 1 wherein said mounting area is formed by two opposing side walls and an end wall.

5. The blood sampling device of claim 4 wherein at least one side wall includes a projecting portion that extends toward the middle of the mounting area and is configured to fit around a specific shape of said test strip.

6. The blood sampling device of claim 1, wherein said adapter further comprises a top portion coupled to the base portion.

7. The blood sampling device of claim 6 wherein the top portion is biased toward the base portion so that when the test strip is removed the top portion moves toward the base portion.

8. The blood sampling device of claim 7 wherein said test strip adapter further comprises grooves formed within said mounting area which are configured to assist in venting air from the test strip to enable blood to readily flow to the mounting area in order to contact said test strip.

9. The blood sampling device of claim 8 further comprising a one-way valve positioned at the blunt cannula and adapted to limit reflux of air into the intravenous line.

10. The blood sampling device of claim 9 wherein said mounting area is formed by two opposing side walls.

11. In a blood monitoring system adapted for monitoring blood parameters, in which the blood monitoring system includes a metering device for metering parameters of the blood, and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, and a test strip having one end configured for contacting the blood sample to permit detecting blood characteristics indicative of a desired blood parameter to be tested, and another end adapted for coupling to the metering device,
- a test strip adapter configured for coupling the test strip in fluid communication with the sampling port of the intravenous line, the test strip adapter comprising:
  - a base portion with a platform which has on a top side of the platform an unsealed mounting area, and the bottom side of said platform being joined to a blunt cannula configured for insertion into the sampling port, the blunt cannula providing fluid communication of a blood sample from the sampling port into the mounting area of the platform;
  - the unsealed mounting area being configured to receive said test strip end comprised of the absorbent material and reagent; and
  - said unsealed mounting area of the platform terminating at a point which is shy of the test strip end adapted for coupling to the metering device, so that a portion of the test strip with the end adapted for coupling to the metering device is exposed so as to be capable of insertion into the metering device without having to remove the test strip from the adapter.

12. The blood sampling device of claim 11 wherein said test strip adapter further comprises grooves formed within said mounting area which are configured to assist in venting air from the test strip to enable blood to readily flow to the mounting area in order to contact said test strip.

13. The blood sampling device of claim 11 further comprising a one-way valve positioned at the blunt cannula and adapted to limit reflux of air into the intravenous line.

14. The blood sampling device of claim 11 wherein said mounting area is formed by two opposing side walls and an end wall.

15. The blood sampling device of claim 14 wherein at least one side wall includes a projecting portion that extends toward the middle of the mounting area and is configured to fit around a specific shape of said test strip.

16. The blood sampling device of claim 11, wherein said adapter further comprises a top portion coupled to the base portion.

17. The blood sampling device of claim 16 wherein the top portion is biased toward the base portion so that when the test strip is removed the top portion moves toward the base portion.

18. The blood sampling device of claim 17 wherein said test strip adapter further comprises grooves formed within said mounting area which are configured to assist in venting air from the test strip to enable blood to readily flow to the mounting area in order to contact said test strip.

19. The blood sampling device of claim 18 further comprising a one-way valve positioned at the blunt cannula and adapted to limit reflux of air into the intravenous line.

20. The blood sampling device of claim 19 wherein said mounting area is formed by two opposing side walls.

21. A method for use in a blood monitoring system adapted for monitoring blood parameters, in which the blood monitoring system includes a metering device for metering parameters of the blood, and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, and a test strip having one end configured for contacting the blood sample to permit detecting blood characteristics indicative of a desired blood parameter to be tested, and another end adapted for coupling to the metering device, the method comprising:
obtaining a test strip adapter configured for coupling the test strip in fluid communication with the sampling port of the intravenous line, the test strip adapter comprising:
a base portion with a platform which has on a top side of the platform an unsealed mounting area, and the bottom side of said platform being joined to a blunt cannula configured for insertion into the sampling port, the blunt cannula providing fluid communication of a blood sample from the sampling port into the mounting area of the platform;
the unsealed mounting area being configured to receive said test strip end comprised of the absorbent material and reagent; and
said unsealed mounting area of the platform terminating at a point that is adapted to permit coupling of the test strip end comprised of electrical leads to the glucometer when the test strip is inserted in said mounting area without having to remove the test strip from the adapter;
inserting the test strip end configured for contacting the blood sample into the mounting area of the base portion;
after blood is withdrawn from the patient into the fluid drawing device and sample port, inserting the blunt cannula into the sample port to obtain a blood sample on the test strip;
removing the test strip adapter with the inserted test strip from the sample port; and
without removing the test strip from the adapter, inserting the exposed end of the test strip into the metering device.

22. A method for use in a blood monitoring system adapted for monitoring blood parameters, in which the blood monitoring system includes a metering device for metering parameters of the blood, and an intravenous system which includes an intravenous line for administering fluids to a patient and through which blood samples are capable of being withdrawn, a sample port connected in the intravenous line and through which fluids are capable of flowing to the patient and through which blood is capable of being withdrawn from the patient, and a fluid drawing device connected into the intravenous line for controlling in one direction flow of fluids into the patient and for controlling in an opposite direction flow of blood from the patient through the sample port and into the fluid drawing device, and a test strip having one end configured for contacting the blood sample to permit detecting blood characteristics indicative of a desired blood parameter to be tested, and another end adapted for coupling to the metering device, the method comprising:
obtaining a test strip adapter configured for coupling the test strip in fluid communication with the sampling port of the intravenous line, the test strip adapter comprising:
a base portion with a platform which has on a top side of the platform an unsealed mounting area, and the bottom side of said platform being joined to a blunt cannula configured for insertion into the sampling port, the blunt cannula providing fluid communication of a blood sample from the sampling port into the mounting area of the platform;
the unsealed mounting area being configured to receive said test strip end comprised of the absorbent material and reagent; and
said unsealed mounting area of the platform terminating at a point that is adapted to permit coupling of the test strip end comprised of electrical leads to the glucometer when the test strip is inserted in said mounting area without having to remove the test strip from the adapter; and
a top portion coupled to the base portion;
inserting the test strip end configured for contacting the blood sample between the top and bottom portions and into the mounting area of the bottom portion;
without removing the test strip from the adapter, inserting the exposed end of the test strip into the metering device;
removing the test strip adapter with the inserted test strip from the sample port; and
removing the test strip from the adapter, and inserting the end of the test strip configured for contacting the blood sample into the metering device.

* * * * *